US008093206B2

(12) United States Patent
Bridon et al.

(10) Patent No.: US 8,093,206 B2
(45) Date of Patent: Jan. 10, 2012

(54) METHODS INVOLVING LONG LASTING SYNTHETIC EXENDIN-4 PEPTIDE CONJUGATES

(75) Inventors: Dominique P. Bridon, San Francisco, CA (US); Benoit L'Archeveque, Dorval (CA); Darren L. Holmes, Anaheim, CA (US); Anouk Leblanc, Montreal (CA); Serge St. Pierre, Ile Bezard (CA)

(73) Assignee: Conjuchem, LLC, Los Angeles, CA (US)

( * ) Notice: Subject to any disclaimer, the term of this patent is extended or adjusted under 35 U.S.C. 154(b) by 0 days.

(21) Appl. No.: 11/304,446

(22) Filed: Dec. 14, 2005

(65) Prior Publication Data
US 2006/0135426 A1    Jun. 22, 2006

Related U.S. Application Data

(60) Continuation of application No. 11/215,967, filed on Aug. 30, 2005, which is a continuation of application No. 11/170,967, filed on Jun. 29, 2005, which is a continuation of application No. 10/722,733, filed on Nov. 25, 2003, now abandoned, which is a continuation of application No. 10/288,340, filed on Nov. 4, 2002, now Pat. No. 6,887,849, which is a division of application No. 09/657,332, filed on Sep. 7, 2000, now Pat. No. 6,514,500, said application No. 10/722,733 is a continuation-in-part of application No. 09/623,548, filed as application No. PCT/US00/13576 on May 17, 2000, now Pat. No. 6,849,714.

(60) Provisional application No. 60/159,783, filed on Oct. 15, 1999, provisional application No. 60/153,406, filed on Sep. 10, 1999, provisional application No. 60/134,406, filed on May 17, 1999.

(51) Int. Cl.
*A61K 38/22* (2006.01)

(52) U.S. Cl. .................................. 514/1.1; 530/308

(58) Field of Classification Search .................. None
See application file for complete search history.

(56) References Cited

U.S. PATENT DOCUMENTS

| 4,462,941 A | 7/1984 | Lee et al. |
| 4,766,106 A | 8/1988 | Katre et al. |
| 5,118,666 A | 6/1992 | Habener |
| 5,120,712 A | 6/1992 | Habener |
| 5,149,782 A | 9/1992 | Chang et al. |
| 5,274,075 A | 12/1993 | Chang |
| 5,424,286 A | 6/1995 | Eng |
| 5,493,007 A | 2/1996 | Burnier et al. |
| 5,545,618 A | 8/1996 | Buckley et al. |
| 5,574,008 A | 11/1996 | Johnson et al. |
| 5,580,853 A | 12/1996 | Sytkowski |
| 5,612,034 A | 3/1997 | Pouletty et al. |
| 5,612,458 A | 3/1997 | Hyldig-Nielsen et al. |
| 5,614,487 A | 3/1997 | Battersby et al. |
| 5,614,492 A | 3/1997 | Habener |
| 5,654,276 A | 8/1997 | Barrett et al. |
| 5,770,570 A | 6/1998 | Paul et al. |
| 5,840,733 A | 11/1998 | Krantz et al. |
| 5,843,440 A | 12/1998 | Pouletty et al. |
| 5,942,620 A | 8/1999 | Krantz et al. |
| 5,958,909 A | 9/1999 | Habener |
| 5,981,488 A | 11/1999 | Hoffmann |
| 6,087,375 A | 7/2000 | Bridon et al. |
| 6,103,233 A | 8/2000 | Pouletty et al. |
| 6,107,489 A | 8/2000 | Krantz et al. |
| 6,133,235 A | 10/2000 | Galloway et al. |
| 6,191,102 B1 | 2/2001 | DiMarchi et al. |
| 6,197,332 B1 | 3/2001 | Zuckermann et al. |
| 6,277,583 B1 | 8/2001 | Krantz et al. |
| 6,277,863 B1 | 8/2001 | Krantz et al. |
| 6,284,725 B1 | 9/2001 | Coolidge et al. |
| 6,329,336 B1 | 12/2001 | Bridon et al. |
| 6,403,324 B1 | 6/2002 | Krantz et al. |
| 6,437,092 B1 | 8/2002 | Ezrin et al. |
| 6,440,417 B1 | 8/2002 | Thibaudeau et al. |
| 6,451,974 B1 | 9/2002 | Hansen |
| 6,500,918 B2 | 12/2002 | Ezrin et al. |
| 6,506,724 B1 | 1/2003 | Hiles et al. |
| 6,514,500 B1 | 2/2003 | Bridon et al. |
| 6,528,486 B1 | 3/2003 | Larsen et al. |
| 6,583,111 B1 | 6/2003 | DiMarchi et al. |
| 6,593,295 B2 | 7/2003 | Bridon et al. |
| 6,602,981 B2 | 8/2003 | Ezrin et al. |
| 6,610,825 B2 | 8/2003 | Ezrin et al. |
| 6,660,716 B1 | 12/2003 | Yakubu-Madus et al. |
| 6,703,359 B1 | 3/2004 | Young et al. |
| 6,706,689 B2 | 3/2004 | Coolidge et al. |
| 6,706,892 B1 | 3/2004 | Ezrin et al. |

(Continued)

FOREIGN PATENT DOCUMENTS

EP    0204447 A2    12/1988

(Continued)

OTHER PUBLICATIONS

U.S. Appl. No. 09/530,891, filed Aug. 16, 2000, Blanchard et al.
U.S. Appl. No. 09/424,571, filed Mar. 7, 2000, Ezrin et al.
Akil, H. et al, (1984) "Endogenous Opioids: Biology and Function," Ann. Rev. Neurosci., 7: 223-255.
Bell, G.J. et al. (1983) "Hamster Preproglucagon Contains the Sequence of Glucagon and Two Related Peptides," Nature, 302: 716-718.
Benhar, Ital et al. (1994) "Pseudomonas Exotoxin A Mutants," *J. of Biological Chem*, 269(18), pp. 13398-13404.
Bergmann, Pierre J. et al. (1985) "Cationlzed Serum Albumin Enhances Response of Cultured Fetal Rat Long Bones to Parathyroid Hormone," Endocrinology, 116(5): 1729-1733.

(Continued)

Primary Examiner — Stacy B. Chen
(74) Attorney, Agent, or Firm — Morrison & Foerster LLP

(57) ABSTRACT

Modified insulinotropic peptides are disclosed. The modified insulinotropic peptides are capable of forming a peptidase stabilized insulinotropic peptide. The modified insulinotropic peptides are capable of forming covalent bonds with one or more blood components to form a conjugate. The conjugates may be formed in vivo or ex vivo. The modified peptides are administered to treat humans with diabetes and other related diseases.

32 Claims, No Drawings

U.S. PATENT DOCUMENTS

| | | | |
|---|---|---|---|
| 6,723,530 B1 | 4/2004 | Drucker | |
| 6,767,887 B1 | 7/2004 | Hoffmann et al. | |
| 6,821,949 B2 | 11/2004 | Bridon et al. | |
| 6,849,714 B1 | 2/2005 | Bridon et al. | |
| 6,858,576 B1 | 2/2005 | Young et al. | |
| 6,861,236 B2 | 3/2005 | Moll et al. | |
| 6,872,700 B1 | 3/2005 | Young et al. | |
| 6,887,470 B1 | 5/2005 | Bridon et al. | |
| 6,887,849 B2 | 5/2005 | Bridon et al. | |
| 6,894,024 B2 | 5/2005 | Coolidge et al. | |
| 6,902,744 B1 | 6/2005 | Koltermann et al. | |
| 6,924,264 B1 | 8/2005 | Prickett et al. | |
| 6,956,026 B2 | 10/2005 | Beeley et al. | |
| 6,989,366 B2 | 1/2006 | Beeley et al. | |
| 6,998,387 B1 | 2/2006 | Goke et al. | |
| 7,090,851 B1 | 8/2006 | Bridon et al. | |
| 7,105,490 B2 | 9/2006 | Beeley et al. | |
| 7,112,567 B2 | 9/2006 | Bridon et al. | |
| 7,115,569 B2 | 10/2006 | Beeley et al. | |
| 7,138,375 B2 | 11/2006 | Beeley et al. | |
| 7,144,854 B1 | 12/2006 | Bridon et al. | |
| 7,157,555 B1 | 1/2007 | Beeley et al. | |
| 7,166,695 B2 | 1/2007 | Krantz et al. | |
| 7,223,725 B1 | 5/2007 | Beeley et al. | |
| 7,226,990 B2 | 6/2007 | Knudsen et al. | |
| 7,256,253 B2 | 8/2007 | Bridon et al. | |
| 7,268,113 B2 | 9/2007 | Bridon et al. | |
| 7,297,761 B2 | 11/2007 | Beeley et al. | |
| 7,307,148 B2 | 12/2007 | Bousquet-Gagnon et al. | |
| 7,419,952 B2 | 9/2008 | Beeley et al. | |
| 2001/0047084 A1 | 11/2001 | Knudsen et al. | |
| 2003/0170250 A1 | 9/2003 | Ezrin et al. | |
| 2004/0053819 A1 | 3/2004 | Dodd et al. | |
| 2004/0127398 A1 | 7/2004 | Bridon et al. | |
| 2004/0138100 A1 | 7/2004 | Bridon et al. | |
| 2004/0156859 A1 | 8/2004 | Ezrin et al. | |
| 2004/0266673 A1 | 12/2004 | Bakis et al. | |
| 2005/0065075 A1 | 3/2005 | Erickson et al. | |
| 2005/0070475 A1 | 3/2005 | Bridon et al. | |
| 2005/0176641 A1 | 8/2005 | Bakis et al. | |
| 2005/0176643 A1 | 8/2005 | Bridon et al. | |
| 2006/0009377 A1 | 1/2006 | Bridon et al. | |
| 2006/0058235 A1 | 3/2006 | Bridon et al. | |
| 2006/0069029 A1 | 3/2006 | Koltermann et al. | |
| 2006/0135428 A1 | 6/2006 | Bridon et al. | |
| 2006/0217304 A1 | 9/2006 | Bridon et al. | |
| 2006/0241019 A1 | 10/2006 | Bridon et al. | |
| 2007/0207958 A1 | 9/2007 | Bridon et al. | |
| 2007/0269863 A1 | 11/2007 | Bridon et al. | |
| 2009/0075890 A1 | 3/2009 | Bridon et al. | |
| 2009/0093408 A1 | 4/2009 | Bridon et al. | |
| 2009/0175821 A1 | 7/2009 | Bridon et al. | |
| 2009/0186819 A1 | 7/2009 | Carrier et al. | |

FOREIGN PATENT DOCUMENTS

| | | |
|---|---|---|
| EP | 0602290 | 6/1994 |
| EP | 0831793 A1 | 4/1998 |
| EP | 0969016 | 1/2000 |
| EP | 0996459 | 5/2000 |
| EP | 1133312 | 9/2001 |
| EP | 1140145 | 10/2001 |
| EP | 1175443 A1 | 1/2002 |
| EP | 1390061 | 2/2004 |
| WO | WO 89/10134 A1 | 11/1989 |
| WO | WO 91/11457 | 8/1991 |
| WO | WO-93/17715 | 9/1993 |
| WO | WO-93/25217 | 12/1993 |
| WO | WO-93/26579 | 12/1993 |
| WO | WO-95/10302 | 4/1995 |
| WO | WO-96/06626 | 3/1996 |
| WO | WO 96/29342 A1 | 9/1996 |
| WO | WO 97/25074 | 1/1997 |
| WO | WO 97/29372 | 1/1997 |
| WO | WO 97/46584 A1 | 12/1997 |
| WO | WO 98/00171 | 1/1998 |
| WO | WO 98/05351 | 2/1998 |
| WO | WO-98/08531 | 3/1998 |
| WO | WO-98/08871 | 3/1998 |
| WO | WO-98/08872 A1 | 3/1998 |
| WO | WO-98/08873 | 3/1998 |
| WO | WO-98/11126 | 3/1998 |
| WO | WO 98/11437 | 3/1998 |
| WO | WO-98/20895 | 5/1998 |
| WO | WO-98/30231 A1 | 7/1998 |
| WO | WO-98/35033 A1 | 8/1998 |
| WO | WO 98/39022 A1 | 9/1998 |
| WO | WO-98/43658 | 10/1998 |
| WO | WO-98/52600 A1 | 11/1998 |
| WO | WO 99/07404 | 2/1999 |
| WO | WO-99/24074 | 5/1999 |
| WO | WO-99/24075 | 5/1999 |
| WO | WO 99/24076 | 5/1999 |
| WO | WO-99/24462 | 5/1999 |
| WO | WO 99/25727 | 5/1999 |
| WO | WO 99/25728 | 5/1999 |
| WO | WO-99/29336 | 6/1999 |
| WO | WO 99/43708 A1 | 9/1999 |
| WO | WO-99/46283 | 9/1999 |
| WO | WO-99/48536 | 9/1999 |
| WO | WO 00/69900 | 5/2000 |
| WO | WO 00/41548 | 7/2000 |
| WO | WO 00/69902 | 11/2000 |
| WO | WO 00/69911 | 11/2000 |
| WO | WO 00/70665 | 11/2000 |
| WO | WO-00/76550 | 12/2000 |
| WO | WO-00/76551 | 12/2000 |
| WO | WO 01/17568 | 3/2001 |
| WO | WO 01/17614 | 3/2001 |
| WO | WO 02/062844 | 8/2002 |
| WO | WO 02/066511 | 8/2002 |
| WO | WO 02/096935 | 12/2002 |
| WO | WO 2004/011498 | 2/2004 |
| WO | WO 2005/012346 | 2/2005 |
| WO | WO 2005/103087 | 11/2005 |
| WO | WO 2005/108418 | 11/2005 |
| WO | WO 2007/053946 | 5/2007 |
| WO | WO 2007/071068 | 6/2007 |

OTHER PUBLICATIONS

Bhargava, Kumaril et al. (1992) "Immobilization of Active Urokinase on Albumin Microspheres: Use of a Chemical Dehydrant and Process Monitoring," *Pharmaceutical Research* 9(6), pp. 776-781.

Delgado, Christina et al. (1992) "The Uses and Properties of PEG-Linked Proteins," *Critical Reviews in Therapeutic Drug Carrier Systems* 9(3,4), pp. 249-304.

Edwards, C. Mark B. et al. (1999) "Glucagon-Like Peptide 1 Has a Physiological Role in the Control of Postprandial Glucose in Humans," Diabetes 48, pp. 86-93.

Edwards, C. Mark B. at al, (2001) "Exendin-4 Reduces Fasting and Postprandial Glucose and Decreases Energy Intake in Healthy Volunteers," *Am. J. Physiol. Endocrinol. Metab* 281, pp. E155-E161.

Eng et al. (1992) "Isolation and Characterization of Exendin-4, an Exendin-3 Analogue, from *Heloderma suspectum* Venom," *J. of Biological Chemistry* 267(11). pp. 7402-7405.

Foa, Piero P. et al. (1991) "Glucagon and Other Products of the Proglucagon Gene: Physiology and Possible Role in the Pathogenesis of Disease." Giomale Italiano Di Dlabetologia 11: (Supplemental) pp. 1-41.

Francis, G. E. et al. (1998) "PEGylation of Cytokines and other Therapeutic Proteins and Peptides: The Importance of Biological Optimisation of Coupling Techniques," *International Journal of Hematology* 68, pp. 1-16.

Gombotz, Wayne R. et al. (1995) "Biodegradable Polymers for Protein and Peptide Drug Delivery," *Bioconjugate Chem.* 6, pp. 332-351.

Goodson, Robert J. et al. (1990) "Site-Directed Pegylation of Recombinant interleukin-2 at Its Glycosylation Site," Bio/Technology 8, pp. 343-346.

Goosen, Mattheus F. A. (1985) "Optimization of Microencapsulation Parameters: Semipermeable Microcapsules as a Bioartificial Pancreas," Biotechnology and Bioengineering vol. XXVII, pp. 146-150.

Heinrich, G. et al. (1984) "Pre-proglucagon messenger ribonucleic acid: nucleotide and encoded amino acid sequences of the rat pancreatic complementary deoxyribonucleic acid," Endocrinology, 115: 2176-2181.

Hirai, Y. et al. (1979) "A new mast cell degranulating peptide "mastoparan" in the venom of *Vespula lewisii*," Chem. Pharm. Bull., 27(8): 1942-1944.

Ishikawa, E. et al. (Oct. 7, 1978) "Enzyme-Labeling with Maleimides and Its Application to the Immunoassay of Peptide Hormones," *Enzyme Labeled Immunoassay of Hormones and Drugs*, Walter deGruyter & Co.., Berlin, New York, pp. 43-57.

Isoai, Atsushi at al. (1993) "A Potent Anti-Metastatic Activity of Tumor Invasion-Inhibiting Factor-2 and Albumin Conjugate," Biochemical and Biophysical Research Communications 192(1), pp. 7-14.

Kapas, S. et al. (1995) "Cloning and Expression of cDNA Encoding a Rat Adrenomedullin Receptor," J. Biol. Chem., 270(43): 25344-25347.

Knusli, C. et al. (1992) "Polyethylene glycol (PEG) modification of granulocyte macrophage colony stimulating factor (GM-CSF) enhances neutrophil priming activity but not colony stimulating activity," British Journal of Haematology, 82: 654-663.

Kolodny, Nelly et al. (1990) "A Conjugation of Synthetic Peptides to Proteins: Quantitation from S-Carboxymethylcystelne Released upon Acid Hydrolysis," Analytical Biochemistry 187, pp. 135-140.

Lopez, L.C. et al. (1983) "Mammalian Pancreatic Preproglucagon Contains three Glucagon-related Peptides," Proc. Natl. Acad. Sci. USA, 80: 5485-5489.

Mao, G. D. et al. (1989) "Superoxide Dismutase: Improving Its Pharmacological Properties by Conjugation with Human Serum Albumin," Biomat., Art. Cells, Artl Org., 17(3), pp. 229-244.

Marburg et al. (1998) "Introduction of the Maleimide Function onto Resin-Bound Peptides: A simple, High yield Process Useful for discriminating among Several Lysines," Bioconjugate Chemistry, 7: 612-616.

Meurer et al. (1999) "Properties of Native and In Vitro Glycosylated Forms of the Glucagon-Like Peptide-1 Receptor Antagonist Exendin (9-39)," *Metabolism* 48(6), pp. 716-724.

Motteson, Kenneth et al., Proceedings of the 8th American Peptide Symposium, 1983, pp. 409-412.

Mumby, S.M. et al. (1986) "Antisera of designed specificity for subunits of guanine nucleotide-binding regulatory proteins," Proc. Natl. Acad. Sci., 83: 265-269.

Oren, Z. et al, (1998) "Mode of Action of Linear Amphipathic α-Helical antimicrobial Peptides," Biopolymers (Peptide Science), 47: 451-463.

Patrias, Karen et al., Biotech Report, 1994/1995, pp. 106-107.

Poznansky, Mark J. et al. (1988) "Growth Hormone-Albumin Conjugates Reduced Renal Toxicity and Altered Plasma Clearance," FEBS Letters.239(1), pp. 18-22.

Qu, Daqing et al. (1996) "A Role for Melanin-Concentrating Hormone in the Central Regulation of Feeding Behaviour," Nature (380), pp. 243-247.

Reubi, J.C. et al. (1982) "Specific High Affinity Binding Sites for Somatostatin-28 on Pancreatic β-Cells: Differences with Brain Somatostatin Receptors," Endocrinology, 110(3): 1049-4051.

Ringsdorf, Helmut (1975) "Structure and Properties of Pharmacologically Active Polymers," J. Polymer Sci: Symposium No. 51, pp. 135-153.

Robberecht, Patrick et al. (1985) "Immunoreactive Helodermin-Like Peptides in Rat: A New Class of Mammalian Neuropeptides Related to Secretin and VIP," Biochemical and Biophysical Research Communications 130(1), pp. 333-342.

Ruiz-Grande, Carmen et al. (1992) "Upolytic Action of Glucagon-Like Peptides In Isolated Rat Adipocytes," *Peptides* (13) pp. 13-16.

Santiago, Julio V. ed. (1996). *Diabetes*, Abstract Book. 56th Annual Meeting and Scientific Sessions, Saturday, Jun. 6-Tuesday Jun. 11, 1996, San Francisco, California. Abstracts 553-556.

Selkoe, D.J. (1993) "Physiological production of the β-amyloid protein and the mechanism of Alzheimer's disease," TINS, 16(10): 403-409.

Siegel et al. (1999) "Biological Activity of GLP-1 analogues with N-terminal modifications," Regulatory Peptides, 79(23): 93-102.

Smith, F.G. et al. (1989) "Atrial natriuretic factor during fetal and postnatal life: A review," J. Dev. Physiol., 12: 55-62.

Stehle, G. et al. (1997) "The Loading Rate Determines Tumor Targeting Properties of Methotrexate-Albumin Conjugates in Rats," Anti-Cancer Drugs, 8: 677-685.

Thim, L. et al. (1998) "Molecules in focus: CART, a new anorectic peptide," Int. J. Biochem. Cell. Biol., 30: 1281-1284.

Turton, M.D. et al. (1996) "A Role for Glucagon-Like-Peptide-1 in the Central Regulation of Feeding," Nature (379), pp. 69-72.

Vilaseca, L. Antonio et al. (1993) "Protein Conjugates of Defined Structure: Synthesis and Use of a New Carrier Molecule," *Bioconjugate Chem.* 4, pp. 515-520.

Yeh, Patrice et al. (1992) "Design of Yeast-Secreted Albumin Derivatives for Human Therapy: Biological and Antiviral Properties of a Serum Albumin-CD4 Genetic Conjugate," *Proc. Natl. Acad. Sci. USA* 89, pp. 1904-1908.

Young, Andrew A. et al. (1999) "Glucose-Lowering and Insulin-Sensitizing Actions of Exendin-4" *Diabetes* 48, pp. 1026-1034.

Zalipsky, Samuel (1995) "Functionalized Poly(ethylene glycol) for Preparation of Biologically Relevant Conjugates," *Bioconjugate Chem.* 6, pp. 150-165.

Zegers, Natty et al. (1990) "An Improved Conjugation Method for Controlled Covalent Coupling of Synthetics Peptides to Proteins Using Glutaraldehyde in a Dialysis Method," *Journal of Immunological Methods* 130, pp. 195-200.

Barragan, Jose M. et al. (1996) "Interactions of exendin-(9-39) with the effects of glucagon-like peptide-1-(7-36) amide and of exendin-4 on arterial blood pressure and heart rate in rats," *Regulatory Peptides*, 67:63-68.

Breton, Jerome et al. (1995) "Prolonged half-life in the circulation of a chemical conjugate between a pro-urokinase derivative and human serum albumin," *Eur. J. Biochem.*, 231: 563-569.

Drucker, Daniel J. (Feb. 1998) "Glucagon-Like Peptides," *Diabetes*, 47(2)159-169.

Eng, John (1996) "Prolonged Effect of Exendin-4 on Hyperglycemia of db/db mice," *Diabetes*, 45:152A (abstract 554).

Hupe-Sodmann, Karin et al. (1997) "Endoproteolysis of Glucagon-like Peptide (GLP)-1 (7-36) amide by Ectopeptidases in RINm5F Cells," *Peptides*, 18(5):625-632.

Raufman, Jean-Pierre (1996) "Bioactive peptides from lizard venoms," *Regulatory Peptides*, 61:1-18.

Ritzel, U. et al. (1998) "A synthetic glucagon-like peptide-1 analog with improved plasma stability," *Journal of Endocrinology*, 159:93-102.

Schirra, Jorg et al. (Apr. 1998) "Exendin(9-39)amide is an Antagonist of Glucagon-like Peptide-1(7-36)amide in Humans," *J. Clin. Invest.*, 101(7):1421-1430.

Syed, Summer et al. (May 1997) "Potent Antithrombin Activity and Delayed Clearance From the Circulation Characterize Recombinant Hirudin Genetically Fused to Albumin," *Blood*, 89(9):3243-3252.

U.S. Appl. No. 60/037,412, filed Feb. 5, 1997, Drucker.
U.S. Appl. No. 60/064,705, filed Nov. 7, 1997, Ezrin et al.
U.S. Appl. No. 60/103,498, filed Oct. 8, 1998, Coolidge et al.
U.S. Appl. No. 60/132,018, filed Apr. 30, 1999, Prickett et al.
U.S. Appl. No. 60/152,681, filed Sep. 7, 1999, Ezrin et al.
U.S. Appl. No. 95/000,276, filed Jul. 9, 2007, ConjuChem Biotechnologies Inc.

Ateshkadi et al., 1993, "Pharmacokinetics of Intraperitoneal, Intravenous, and Subcutaneous Recombinant Human Erythropoietin in Patients on Continuous Ambulatory Peritoneal Dialysis," *Am. J. Kidney Dis.* 21(6):635-642.

Binder et al., 1984, "Insulin Pharmacokinetics," *Diabetes Care* 7:188-199.

Coleman, 1978, "Obese and Diabetes: Two Mutant Genes Causing Diabetes-Obesity Syndromes in Mice," *Diabetologia* 14:141-148.

Davis et al., 1991, "Reduction of Immunogenicity and Extension of Circulating Half-Life of Peptides and Proteins," *Peptide and Protein and Drug Delivery*, Marcel Dekker, Inc., New York, 831-864.

Eng et al., 1990, "Purification and Structure of Exendin-3, a New Pancreatic Secretagogue Isolated from *Heloderma horridum* Venom," *J. Biol. Chem.* 265:20259-20262.

Göke et al., 1989, "Characterization of the Receptor for Glucagon-like-peptide-1(7-36)amide on Plasma Membranes from Rat Insulinoma-derived Cells by Covalent Cross-Linking," *J. Mol. Endocrinol.* 2:93-98.

Göke et al., 1992, "Solubilization of Active GLP-1 (7-36)amide Receptors From RINm5F Plasma Membranes," *FEBS Lett.* 300:232-236.

Göke et al., 1993, "Exendin-4 is a High Potency Agonist and Truncated Exendin-(9-39)-amide an Antagonist at the Glucagon-like Peptide 1-(7-36)-amide Receptor of Insulin-secreting β-Cells," *J. Biol. Chem.* 268(26):19650-19655.

Göke et al., 1995, "Distribution of GLP-1 Binding Sites in the Rat Brain: Evidence that Exendin-4 is a Ligand of Brain GLP-1 Binding Sites," *Eur. J. Neurosci.* 7:2294-2300.

Grieg et al., Jan. 1999, "Once Daily Injection of Exendin-4 to Diabetic Mice Achieves Long-Term Beneficial Effects of Blood Glucose Concentrations," *Diabetologia* 42:45-50.

Hoshino et al., 1984, "Primary Structure of Helodermin, a VIP-Secretin-Like Peptide Isolated from Gila Monster Venom," *FEBS Lett.* 178:233-239.

Kelly et al., 1996, "Acute Effects of Intraperitoneal Versus Subcutaneous Insulin Delivery on Glucose Homeostasis in Patients with NIDDM. Veterans Affairs Implantable Insulin Pump Study Group," *Diabetes Care* 11:1237-1242.

Mattson et al., 1993, "A Practical Approach to Crosslinking," *Mol. Biol. Reports* 17:167-183.

Paige et al., 1995, "Prolonged Circulation of Recombinant Human Granulocyte-Colony Stimulating Factor by Covalent Linkage to Albumin Through a Heterobifunctional Polyethylene Glycol," *Pharmaceutical Research* 12(12):1883-1888.

Petrella et al., May 1999, "Development and Validation of an Immunoradiometric Assay (IRMA) for the Quantitation of Exendin-4 in Plasma and Its Application to Preclinical Toxicity and Phase I Clinical Evaluations," Diabetes 48:A425.

Poznansky & Juliano, 1984, "Biological Approaches to the Controlled Delivery of Drugs: A Critical Review," *Pharmacological Reviews* 36:277-335.

Richter et al., 1991, "Characterization of Glucagon-Like Peptide-1(7-36)amide Receptors of Rat Lung Membranes by Covalent Cross-Linking," *FEBS Lett.* 280:247-250.

Schmidtler et al., 1994, "Rat Parietal Cell Receptors for GLP-1-(7-36) Amide: Northern Blot, Cross-Linking, and Radioligand Binding," Am. J. Physiol. 267:G423-432.

Thibaudeau et al., 2006, "CJC-1134-PC: An Exendin-4 Conjugate with Extended Pharmacodynamic Profiles in Rodents," *American Diabetes Association 66th Scientific Sessions,* Washington D.C., Jun. 9-13, 2006 (poster 434-P).

Vandermeers et al., 1984, "Purification of a Novel Pancreatic Secretory Factor (PSF) and a Novel Peptide with VIP- and Secretin-like Properties (Helodermin) from Gila Monster Venom," *FEBS Lett.* 166:273-276.

Vandermeers et al., 1987, "Chemical, Immunological and Biological Properties of Peptides Like Vasoactive-Intestinal-Peptide and Peptide-Histidine-Isoleucinamide Extracted from the Venom of Two Lizards (*Heloderma horridum* and *Heloderma suspectum*)," *Eur. J. Biochem.* 164:321-327.

Haak, 1999, "New Developments in the Treatment of Type I Diabetes Mellitus," *Exp. Clin. Endocrinol. Diabetes* 107(Supp. 3):S108-113.

Harlow & Lane, 1988, *Antibodies: A Laboratory Manual,* pp. 101, 129.

Request for Inter Partes Reexamination Pursuant to 35 U.S.C. § 311 and 37 C.F.R. 1.913, dated Jul. 9, 2007, for Reexamination of Prickett et al., U.S. Patent No. 6,924,264 B1, Reexamination Request Control No. 95/000,276.

Declaration of Mark J. Poznansky, dated Jul. 6, 2007, for Reexamination of Prickett et al., U.S. Patent No. 6,924,264 B1, Reexamination Request Control No. 95/000,276.

Second Declaration of Mark J. Poznansky, dated Jul. 6, 2007, for Reexamination of Prickett et al., U.S. Patent No. 6,924,264 B1, Reexamination Request Control No. 95/000,276.

Declaration of Omar Quraishi, dated Jul. 6, 2007, for Reexamination of Prickett et al., U.S. Patent No. 6,924,264 B1, Reexamination Request Control No. 95/000,276.

Order Granting Request for Inter Partes Reexamination, dated Oct. 3, 2007, for Reexamination of Prickett et al., U.S. Patent No. 6,924,264 B1, Reexamination Request Control No. 95/000,276.

Non-final Office Action, dated Jan. 17, 2008, for Reexamination of Prickett et al., U.S. Patent No. 6,924,264 B1, Reexamination Request Control No. 95/000,276.

Response Pursuant to 35 U.S.C. § 304 and 37 C.F.R. 1.111, dated Apr. 16, 2008, for Reexamination of Prickett et al., U.S. Patent No. 6,924,264 B1, Reexamination Request Control No. 95/000,276.

Declaration of Andrew Young, M.D., Ph.D., Pursuant to 37 C.F.R. § 1.132, dated Apr. 15, 2008, for Reexamination of Prickett et al., U.S. Patent No. 6,924,264 B1, Reexamination Request Control No. 95/000,276.

Declaration of John Herich Pursuant to 37 C.F.R. § 1.132, dated Apr. 15, 2008, for Reexamination of Prickett et al., U.S. Patent No. 6,924,264 B1, Reexamination Request Control No. 95/000,276.

Comments Pursuant to 37 C.F.R. § 1.947 by Third Party Requester, dated May 15, 2008, for Reexamination of Prickett et al., U.S. Patent No. 6,924,264 B1, Reexamination Request Control No. 95/000,276.

Second Declaration of Omar Quraishi, dated May 15, 2008, for Reexamination of Prickett et al., U.S. Patent No. 6,924,264 B1, Reexamination Request Control No. 95/000,276.

Third Declaration of Mark J. Poznansky, dated May 14, 2008, for Reexamination of Prickett et al., U.S. Patent No. 6,924,264 B1, Reexamination Request Control No. 95/000,276.

Action Closing Prosecution, dated Mar. 5, 2009, for Reexamination of Prickett et al., U.S. Patent No. 6,924,264 B1, Reexamination Request Control No. 95/000,276.

Amendment and Response Pursuant to 37 C.F.R. § 1.195(a), dated May 5, 2009, for Reexamination of Prickett et al., U.S. Patent No. 6,924,264 B1, Reexamination Request Control No. 95/000,276.

Second Declaration of John Herich Pursuant to 37 C.F.R. § 1.132, dated Apr. 30, 2009, for Reexamination of Prickett et al., U.S. Patent No. 6,924,264 B1, Reexamination Request Control No. 95/000,276.

Declaration of John Eng. M.D., Pursuant to 37 C.F.R. § 1.132, dated Apr. 23, 2009, for Reexamination of Prickett et al., U.S. Patent No. 6,924,264 B1, Reexamination Request Control No. 95/000,276.

Declaration of Rüdiger Göke and Burkhard Göke, Pursuant to 37 C.F.R. § 1.132, dated May 2, 2009, for Reexamination of Prickett et al., U.S. Patent No. 6,924,264 B1, Reexamination Request Control No. 95/000,276.

Comments Pursuant to 37 C.F.R. § 1.951(b) by Third Party Requester, dated Jun. 3, 2009, for Reexamination of Prickett et al., U.S. Patent No. 6,924,264 B1, Reexamination Request Control No. 95/000,276.

Right of Appeal Notice (37 C.F.R. § 1.953), dated Dec. 17, 2009, for Reexamination Request Control No. 95/000,276.

Petition Under 37 C.F.R. § 1.182 Requesting Continued Reexamination, dated Jan. 6, 2010, for Reexamination Request Control No. 95/000,276.

Comments on Petition Under 37 C.F.R. § 1.182 Requesting Continued Reexamination, dated Feb. 4, 2010, for Reexamination Request Control No. 95/000,276.

Decision on Petition to Continue Inter Partes Reexamination Proceedings, dated Mar. 16, 2010, for Reexamination Request Control No. 95/000,276.

Comments Pursuant to 37 CFR 1.947 by Third Party Requester to Patent Owner's Amendment and Response filed May 5, 2009, dated Apr. 14, 2010, for Reexamination Request Control No. 95/000,276.

Pohl, M. et al. (Apr. 17, 1998). "Molecular Cloning of the Helodermin and Exendin-4 cDNAs in the Lizard: Relationship to Vasoactive Intestinal Polypeptide/Pituitary Adenylate Cyclase Activating Polypeptide and Glucagon-Like Peptide 1 and Evidence Against the Existence of Mammalian Homologues," *Journal of Biological Chemistry* 273(16):9778-9784.

Non-final Office Action mailed Jun. 26, 2007, for U.S. Appl. No. 11/170,967, filed Jun. 29, 2005, 11 pages.

Final Office Action mailed Mar. 26, 2008, for U.S. Appl. No. 11/170,967, filed Jun. 29, 2005, 8 pages.

Ex Parte Quayle mailed Sep. 10, 2008, for U.S. Appl. No. 11/170,967, filed Jun. 29, 2005, 6 pages.

Ex Parte Quayle mailed Dec. 31, 2008, for U.S. Appl. No. 11/170,967, filed Jun. 29, 2005, 4 pages.

Non-final Office Action mailed May 22, 2009, for U.S. Appl. No. 11/170,967, filed Jun. 29, 2005, 7 pages.

Final Office Action mailed Dec. 7, 2009, for U.S. Appl. No. 11/170,967, filed Jun. 29, 2005, 7 pages.
Final Office Action mailed Jun. 29, 2010, for U.S. Appl. No. 11/170,967, filed Jun. 29, 2005, 7 pages.
Non-final Office Action mailed Jun. 26, 2007, for U.S. Appl. No. 11/215,967, filed Aug. 30, 2005, 12 pages.
Final Office Action mailed Mar. 20, 2008, for U.S. Appl. No. 11/215,967, filed Aug. 30, 2005, 8 pages.
Ex Parte Quayle mailed Sep. 9, 2008, for U.S. Appl. No. 11/215,967, filed Aug. 30, 2005, 6 pages.
Ex Parte Quayle mailed Dec. 31, 2008, for U.S. Appl. No. 11/215,967, filed Aug. 30, 2005, 4 pages.
Non-final Office Action mailed May 22, 2009, for U.S. Appl. No. 11/215,967, filed Aug. 30, 2005, 6 pages.
Final Office Action mailed Dec. 7, 2009, for U.S. Appl. No. 11/215,967, filed Aug. 30, 2005, 7 pages.
Final Office Action mailed Jun. 28, 2010, for U.S. Appl. No. 11/215,967, filed Aug. 30, 2005, 7 pages.
Non-final Office Action mailed May 18, 2010, for U.S. Appl. No. 12/221,553, filed Aug. 1, 2008, 14 pages.
Final Office Action mailed Feb. 7, 2011, for U.S. Appl. No. 12/221,553, filed Aug. 1, 2008, 9 pages.
Notice of Appeal Pursuant to 37 C.F.R. § 41.61 (a)(I), dated Jan. 6, 2010, for U.S. Patent No. 6,924,261 B1, Reexamination Request Control No. 95/000,276, 2 pages.
Petition Under 37 C.F.R. § 1.182, Requesting Entry of an Application Data Sheet (ADS), dated Jun. 30, 2008, for U.S. Appl. No. 10/722,733, 30 pages.
Decision on Petition Under 37 C.F.R. § 1.182, Requesting Entry of an Application Data Sheet (ADS), dated Sep. 2, 2008, for U.S. Appl. No. 10/722,733, 2 pages.
First Request for Reconsideration of Decision on Petition Under 37 C.F.R. § 1.182, dated Oct. 30, 2008, for U.S. Appl. No. 10/722,733, 4 pages.
Decision on First Request for Reconsideration of Decision on Petition Under 37 C.F.R. § 1.182, dated Dec. 19, 2008, for U.S. Appl. No. 10/722,733, 2 pages.
Second Request for Reconsideration of Decision on Petition Under 37 C.F.R. § 1.182, dated Feb. 5, 2009, for U.S. Appl. No. 10/722,733, 7 pages.
Decision on Second Request for Reconsideration of Decision on Petition Under 37 C.F.R. § 1.182, dated May 19, 2009, for U.S. Appl. No. 10/722,733, 3 pages.
Third Request for Reconsideration of Decision on Petition Under 37 C.F.R. § 1.182, dated Jul. 16, 2009, for U.S. Appl. No. 10/722,733, 4 pages.
Decision on Third Request for Reconsideration of Decision on Petition Under 37 C.F.R. § 1.182, dated Mar. 15, 2010, for U.S. Appl. No. 10/722,733, 4 pages.
4$^{th}$ Petition to Accept an Unintentionally Delayed Claim for Priority Under 37 C.F.R. § 1.78 (A)(3) with accompanied exhibits, and Petition under 37 C.F.R. § 1.182 to request expedite review of petition under 37 C.F.R. § 1.78 (A)(3), filed with the U.S. Patent and Trademark Office on May 13, 2010, for U.S. Appl. No. 10/722,733, 29 pages.
Decision on 4$^{th}$ Renewed Petition Under 37 C.F.R. § 1.78 (A)(3), and Petition under 37 C.F.R. § 1.182, mailed Jun. 10, 2010, for U.S. Appl. No. 10/722,733, 3 pages.
5$^{th}$ Renewed Petition Under 37 C.F.R. § 1.78 (A)(3), and Petition under 37 C.F.R. § 1.182 to Request Expedite Review of Petition under 37 C.F.R. § 1.78 (A)(3), filed with the U.S. Patent and Trademark Office on Aug. 3, 2010, for U.S. Appl. No. 10/722,733, 10 pages.
Decision on Renewed Petition Under 37 C.F.R. § 1.78 (A)(3), and Petition under 37 C.F.R. § 1.182, mailed Sep. 10, 2010, for No. 10/722,733, 6 pages.
Comments on Petition under 37 C.F.R. § 1.182 Requesting Continued Reexamination, dated Feb. 4, 2010, for U.S. Patent No. 6,924,261 B1, Reexamination Request Control No. 95/000,276, 46 pages.
Comments Pursuant to 37 C.F.R. § 1.947 by Third Party Request, dated Apr. 14, 2010, for U.S. Patent No. 6,924,261 B1, Reexamination Request Control No. 95/000,276, 50 pages.
Response Pursuant to 37 C.F.R. § 1.951(a), dated Apr. 18, 2011, for U.S. Patent No. 6,924,261 B1, Reexamination Request Control No. 95/000,276, 12 pages.
Third Party Comments after Patent Owner Response Pursuant to 37 C.F.R. § 1.951, dated May 18, 2011, for U.S. Patent No. 6,924,261 B1, Reexamination Request Control No. 95/000,276, 20 pages.

SEQUENCE LISTING

<160> NUMBER OF SEQ ID NOS: 48

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic Peptide

```
<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(22)
<223> OTHER INFORMATION: Xaa represents Lys or Arg

<400> SEQUENCE: 3

Ser Tyr Leu Glu Gly Gln Ala Ala Lys Glu Phe Ile Ala Trp Leu Val
1               5                   10                  15

Xaa Gly Arg Xaa Gly Arg
            20

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Ser Asp Val Ser
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 5

Thr Ser Asp Val Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Phe Thr Ser Asp Val Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Thr Phe Thr Ser Asp Val Ser
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gly Thr Phe Thr Ser Asp Val Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Glu Gly Thr Phe Thr Ser Asp Val Ser
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Ala Glu Gly Thr Phe Thr Ser Asp Val Ser
1               5                   10

<210> SEQ ID NO 11
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 11

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

His Gly Glu Gly Thr Phe Thr Ser Asp Leu Ser Lys Gln Met Glu Glu
1               5                   10                  15

Ala Val Arg Leu Phe Ile Glu Trp Leu Lys Asn Gly Gly Pro Tyr
                20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Tyr
                20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15
```

```
Asp Leu Ser Lys Gln Met Glu Glu Ala Val Arg Leu Met Ile Glu
1               5                  10                  15

Trp Leu Lys Asn Gly Gly Pro Ser Ser Gly Ala Pro Pro Pro Ser
             20                  25                  30
```

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

```
His Asp Glu Phe Glu Arg His Ala Glu Gly Thr Phe Thr Ser Asp Val
1               5                  10                  15

Ser Ser Tyr Leu Glu Gly Gln Ala Ala Lys Glu Phe Ile Ala Trp Leu
             20                  25                  30

Val Lys Gly Arg Lys
         35
```

<210> SEQ ID NO 17
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

```
His Ala Glu Gly Thr Phe Thr Ser Asp Val Ser Ser Tyr Leu Glu Gly
1               5                  10                  15

Gln Ala Ala Lys Glu Phe Ile Ala Trp Leu Val Lys Gly Arg Lys
             20                  25                  30
```

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

```
His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Ser
             20                  25                  30

Ser Gly Ala Pro Pro Pro Ser Lys
         35                  40
```

<210> SEQ ID NO 19
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

```
His Ser Asp Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Ser
             20                  25                  30
```

```
Ser Gly Ala Pro Pro Ser Lys
        35                  40

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

His Gly Glu Gly Thr Phe Thr Ser Asp Leu Ser Lys Glu Met Glu Glu
1               5                   10                  15

Glu Val Arg Leu Phe Ile Glu Trp Leu Lys Asn Gly Gly Pro Tyr
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

His Gly Glu Gly Thr Phe Thr Ser Asp Leu Ser Lys Glu Met Glu Glu
1               5                   10                  15

Glu Val Arg Leu Phe Ile Glu Trp Leu Lys Asn Gly Gly Tyr
            20                  25                  30

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Asp Leu Ser Lys Gln Met Glu Glu Glu Ala Val Arg Leu Phe Ile Glu
1               5                   10                  15

Trp Leu Lys Gly Gly Pro Ser Ser Gly Pro Pro Pro Ser
            20                  25

<210> SEQ ID NO 23
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: 31
<223> OTHER INFORMATION: Xaa represents Tyr-amide

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa
            20                  25                  30

<210> SEQ ID NO 24
<211> LENGTH: 31
<212> TYPE: PRT
<213> ORGANISM: Artificial Sequence
```

```
<220> FEATURE:
<223> OTHER INFORMATION: Description of Artificial Sequence: Synthetic
      Peptide
<221> NAME/KEY: MOD_RES
<222> LOCATION: 31
<223> OTHER INFORMATION: Xaa represents Ser-amide

<400> SEQUENCE: 24

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Xaa
            20                  25                  30

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 37
<223> OTHER INFORMATION: Xaa represents Lys (E-MPA)-NH2-5TFA and where
      "E" represents Epsilon

<400> SEQUENCE: 25

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Xaa
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 37
<223> OTHER INFORMATION: Xaa represents Lys (E-AEEA-AEEA-MPA)-NH2-5TFA
      and where "E" represents Epsilon

<400> SEQUENCE: 26

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Xaa
        35

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 31
<223> OTHER INFORMATION: Xaa represents Lys (E-MPA)-NH2-4TFA and where
      "E" represents Epsilon

<400> SEQUENCE: 27

His Ala Glu Gly Thr Phe Thr Ser Asp Val Ser Ser Tyr Leu Glu Gly
1               5                   10                  15
```

```
Gln Ala Ala Lys Glu Phe Ile Ala Trp Leu Val Lys Gly Arg Xaa
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 31
<223> OTHER INFORMATION: Xaa represents Lys (E-AEEA-AEEA-MPA)-NH2-4TFA
      and where "E" represents Epsilon

<400> SEQUENCE: 28

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 2
<223> OTHER INFORMATION: Xaa represents D-Ala
<221> NAME/KEY: MOD_RES
<222> LOCATION: 31
<223> OTHER INFORMATION: Xaa represents Lys (E-MPA)-NHH2-4TFA and where
      "E" represents Epsilon

<400> SEQUENCE: 29

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 2
<223> OTHER INFORMATION: Xaa represents D-Ala
<221> NAME/KEY: MOD_RES
<222> LOCATION: 31
<223> OTHER INFORMATION: Xaa represents Lys (E-AEEA-AEEA-MPA)-NH2-4TFA
      and where "E" represents Epsilon

<400> SEQUENCE: 30

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 31
<211> LENGTH: 40
<212> TYPE: PRT
<213> ORGANISM: Artificial Sequence
<220> FEATURE:
<223> OTHER INFORMATION: Description of Artificial Sequence: Synthetic
```

```
                            Peptide
<221> NAME/KEY: MOD_RES
<222> LOCATION: 40
<223> OTHER INFORMATION: Xaa represents Lys (E-MPA)-NH2-5TFA and where
      "E" represents Epsilon

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 32
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 40
<223> OTHER INFORMATION: Xaa represents Lys (E-AEEA-AEEA-MPA)-NH2-5TFA
      and where "E" represents Epsilon

<400> SEQUENCE: 32

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 33
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 40
<223> OTHER INFORMATION: Xaa represents Lys (E-MPA)-NH2-5TFA and where
      "E" represents Epsilon

<400> SEQUENCE: 33

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 34
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide
```

```
<221> NAME/KEY: MOD_RES
<222> LOCATION: 40
<223> OTHER INFORMATION: Xaa represents Lys (E-AEEA-AEEA-MPA)-NH2-5TFA
      and where "E" represents Epsilon

<400> SEQUENCE: 34

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 32
<223> OTHER INFORMATION: Xaa represents Tyr-amide

<400> SEQUENCE: 35

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Xaa
            20                  25                  30

<210> SEQ ID NO 36
<211> LENGTH: 40
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 40
<223> OTHER INFORMATION: Xaa represents Lys (E-AEEA-MPA)-NH2 and where
      "E" represents Epsilon

<400> SEQUENCE: 36

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 20
<223> OTHER INFORMATION: Xaa represents Lys (E-MPA) and where "E"
      represents Epsilon

<400> SEQUENCE: 37
```

```
His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Lys Gly Arg
            20                  25                  30
```

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 30
<223> OTHER INFORMATION: Xaa represents Arg (EDA-MPA)

<400> SEQUENCE: 38

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa
            20                  25                  30
```

<210> SEQ ID NO 39
<211> LENGTH: 39
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 39
<223> OTHER INFORMATION: Xaa represents Ser (EDA-MPA)

<400> SEQUENCE: 39

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Xaa
        35
```

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His (Boc)
<221> NAME/KEY: MOD_RES
<222> LOCATION: 20
<223> OTHER INFORMATION: Xaa represents Lys (Aloc)
<221> NAME/KEY: MOD_RES
<222> LOCATION: 30
<223> OTHER INFORMATION: Xaa represents Arg (PS) and where "PS"
      represents Rink Amide MBHA resin

<400> SEQUENCE: 40

```
Xaa Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Lys Gly Xaa
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His (Boc)
<221> NAME/KEY: MOD_RES
<222> LOCATION: 30
<223> OTHER INFORMATION: Xaa represents Arg (PS) and where "PS"
      represents Rink Amide MBHA resin

<400> SEQUENCE: 41

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His (Boc)
<221> NAME/KEY: MOD_RES
<222> LOCATION: 20
<223> OTHER INFORMATION: Xaa represents Lys (E-MPA) and where "E"
      represents Epsilon
<221> NAME/KEY: MOD_RES
<222> LOCATION: 30
<223> OTHER INFORMATION: Xaa represents Arg (PS) and where "PS"
      represents Rink Amide MBHA resin

<400> SEQUENCE: 42

Xaa Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Lys Gly Xaa
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
```

<223> OTHER INFORMATION: Xaa represents His (Boc)
<221> NAME/KEY: MOD_RES
<222> LOCATION: 30
<223> OTHER INFORMATION: Xaa represents Arg (SASRIN) where "SASRIN"
      represents super acid sensitive resin

<400> SEQUENCE: 43

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His (Boc)

<400> SEQUENCE: 44

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His (Boc)
<221> NAME/KEY: MOD_RES
<222> LOCATION: 30
<223> OTHER INFORMATION: Xaa represents Arg (EDA-MPA)

<400> SEQUENCE: 45

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa
            20                  25                  30

<210> SEQ ID NO 46
<211> LENGTH: 39
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His(Boc)
<221> NAME/KEY: MOD_RES
<222> LOCATION: 39
<223> OTHER INFORMATION: Xaa represents Ser (SASRIN) where "SASRIN"
      represents super acid sensitive resin

```
<400> SEQUENCE: 46

Xaa Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Xaa
        35

<210> SEQ ID NO 47
<211> LENGTH: 39
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His(Boc)

<400> SEQUENCE: 47

Xaa Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 48
<211> LENGTH: 39
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: MOD_RES
<222> LOCATION: 1
<223> OTHER INFORMATION: Xaa represents His(Boc)
<221> NAME/KEY: MOD_RES
<222> LOCATION: 39
<223> OTHER INFORMATION: Xaa represents Ser (EDA-MPA)

<400> SEQUENCE: 48

Xaa Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Xaa
        35
```

METHODS INVOLVING LONG LASTING SYNTHETIC EXENDIN-4 PEPTIDE CONJUGATES

RELATED APPLICATIONS

This application is a continuation of U.S. application Ser. No. 11/215,967, filed Aug. 30, 2005, which is a continuation of U.S. application Ser. No. 11/170,967, filed Jun. 29, 2005, which is a continuation of U.S. application Ser. No. 10/722,733, filed Nov. 25, 2003, now abandoned, which is a continuation of U.S. application Ser. No. 10/288,340, filed Nov. 4, 2002, now U.S. Pat. No. 6,887,849, which is a divisional of U.S. patent application Ser. No. 09/657,332, filed Sep. 7, 2000, now U.S. Pat. No. 6,514,500, which claims the benefit under 35 USC 119(e) of U.S. Provisional Application No. 60/159,783, filed Oct. 15, 1999. U.S. application Ser. No. 10/722,733 is also a continuation of U.S. application Ser. No. 09/623,548, filed Sep. 5, 2000, now U.S. Pat. No. 6,849,714 which is a National Stage of PCT/US00/13576, filed May 17, 2000 which claims the benefit under 35 USC 119(e) of U.S. Provisional Application Nos. 60/159,783, filed Oct. 15, 1999, 60/153,406, filed Sep. 10, 1999, and 60/134,406, filed May 17, 1999. The contents of all the above cited patents and patent applications are hereby incorporated by reference in their entirety.

FIELD OF THE INVENTION

This invention relates to modified insulinotropic peptides. In particular, this invention relates to modified glucagon like peptides and exendin peptides with long duration of action for the treatment of diabetes and other insulinotropic peptide related diseases, gastrointestinal function and activities associated with glucagon levels.

BACKGROUND OF THE INVENTION

The insulinotropic peptide hormone glucagon-like peptide (GLP-1) has been implicated as a possible therapeutic agent for the management of type 2 non-insulin-dependent diabetes mellitus as well as related metabolic disorders, such as obesity. Other useful insulinotropic peptides include exendin 3 and exendin 4. While useful, GLP-1, exendin 3 and exendin 4 suffer from limited duration of action associated with short plasma half-lifes in vivo, mainly due to rapid serum clearance and proteolytic degradation. The enzyme responsible for the degradation of GLP-1. dipeptidyl peptidase IV, has been identified. Extensive work has been done in attempts to inhibit the peptidase or to modify GLP1 in such a way that its degradation is slowed down while still maintaining biological activity. Despite these extensive efforts, a long lasting, active GLP-1 has not been produced. As such, the diabetic community has a tremendous need for improved GLP-1, exendin 3 and exendin 4 peptides.

There is thus a need to modify GLP-1, exendin 3, exendin 4 and other insulinotropic peptides to provide longer duration of action in vivo, while maintaining their low toxicity and therapeutic advantages.

SUMMARY OF THE INVENTION

In order to meet those needs, the present invention is directed to modified insulinotropic peptides (ITPs). This invention relates to novel chemically reactive derivatives of insulinotropic peptides that can react with available functionalities on cellular carriers including mobile blood proteins to form covalent linkages. Specifically, the invention relates to novel chemically reactive derivatives of insulinotropic peptides such as glucagon like peptide (GLP) and exendin 3 and exendin 4 that can react with available functionalities on mobile blood proteins to form covalent linkages. The invention also relates to novel chemically reactive derivatives or analogs of insulinotropic peptides that can react with available functionalities on mobile blood proteins to form covalent linkages.

The present invention relates to modified insulinotropic peptides comprising a reactive group which reacts with amino groups, hydroxyl groups or thiol groups on blood compounds to form stable covalent bonds.

The present invention relates to an insulinotropic hormone comprising a modified fragment of GLP-1 and derivatives thereof, especially GLP-1 (7-36) amide. The invention additionally pertains to the therapeutic uses of such compounds, and especially to the use of modified GLP-1 (7-36) amide for the treatment of maturity onset diabetes mellitus (type II diabetes).

The present invention further relates to modified Exendin 3 and Exendin 4 fragments and therapeutic uses of such compounds.

In particular, the present invention is directed to GLP-1(1-36)-Lys$^{37}$ ($\epsilon$-MPA)-NH$_2$, GLP-1 (1-36)-Lys$^{37}$ ($\epsilon$-AAEA-AEEA-MPA)-NH$_2$, GLP-1 (7-36)-Lys$^{37}$ ($\epsilon$-MPA)-NH$_2$; GLP-1 (7-36)-Lys$^{37}$-($\epsilon$-AEEA-AEEA-MPA)-NH$_2$; D-Ala$^2$ GLP-1 (7-36)-Lys$^{37}$ ($\epsilon$-MPA)-NH$_2$; Exendin-4 (1-39)-Lys$^{40}$ ($\epsilon$-MPA)—NH$_2$, Exendin-4 (1-39)-Lys$^{40}$ ($\epsilon$-AEEA-AEEA-MPA)-NH$_2$; Exendin-3 (1-39)-Lys$^{40}$ ($\epsilon$-MPA)-NH$_2$; Exendin-3 (1-39)-Lys$^{40}$ ($\epsilon$-AEEA-AEEA-MPA)-NH$_2$; Lys$^{26}$($\epsilon$-MPA)GLP-1(7-36)-NH$_2$; GLP-1 (7-36)-EDA-MPA and Exendin-4 (1-39)-EDA-MPA.

The present invention further relates to compositions comprising the derivatives of the insulinotropic peptides and the use of the compositions for treating diabetes in humans.

The invention further pertains to a method for enhancing the expression of insulin which comprises providing to a mammalian pancreatic Beta-type islet cell an effective amount of the modified insulinotropic peptides disclosed above.

The invention further pertains to a method for treating maturity-onset diabetes mellitus which comprises administration of an effective amount of the insulinotropic peptides discussed above to a patient in need of such treatment.

The invention further pertains to the treatment of other insulinotropic peptide related diseases and conditions with the modified insulinotropic peptides of the invention.

DETAILED DESCRIPTION OF THE INVENTION

Definitions

To ensure a complete understanding of the invention the following definitions are provided:

Insulinotropic Peptides: insulinotropic peptides (ITPs) are peptides with insulinotropic activity. Insulinotropic peptides stimulate, or cause the stimulation of, the synthesis or expression of the hormone insulin. Such peptides include precursors, analogues, fragments of peptides such as Glucagon-like peptide, exendin 3 and exendin 4 and other peptides with insulinotropic activity.

Glucagon-Like Peptide: Glucagon-Like Peptide (GLP) and GLP derivatives are intestinal hormones which generally simulate insulin secretion during hyperglycemia, suppresses glucagon secretion, stimulates (pro) insulin biosynthesis and decelerates gastric emptying and acid secretion. Some GLPs and GLP derivatives promote glucose uptake by cells but do not simulate insulin expression as disclosed in U.S. Pat. No. 5,574,008 which is hereby incorporated by reference.

Exendin 3 and Exendin 4 Peptides: Exendin 3 and exendin 4 peptides and peptide derivatives are 39 amino acid peptides which are approximately 53% homologous to GLP-1 and have insulinotropic activity.

Reactive Groups: Reactive groups are chemical groups capable of forming a covalent bond. Such reactive agents are coupled or bonded to an insulinotropic peptide of interest to form a modified insulinotropic peptide. Reactive groups will generally be stable in an aqueous environment and will usually be carboxy, phosphoryl or convenient acyl group, either as an ester or a mixed anhydride, or an imidate, thereby capable of forming a covalent bond with functionalities such as an amino group, a hydroxy or a thiol at the target site on mobile blood components. For the most part, the esters will involve phenolic compounds, or be thiol esters, alkyl esters, phosphate esters, or the like. Reactive groups include succinimidyl and maleimido groups.

Functionalities: Functionalities are groups on blood components to which reactive groups on modified insulinotropic peptides react to form covalent bonds. Functionalities include hydroxyl groups for bonding to ester reactive entities; thiol groups for bonding to malemides and maleimido groups, imidates and thioester groups; amino groups for bonding to carboxy, phosphoryl or acyl groups on reactive entities and carboxyl groups for bonding to amino groups. Such blood components include blood proteins.

Linking Groups: Linking groups are chemical moieties that link or connect reactive groups to ITPs. Linking groups may comprise one or more alkyl groups such as methyl, ethyl, propyl, butyl, etc. groups, alkoxy groups, alkenyl groups, alkynyl groups or amino group substituted by alkyl groups, cycloalkyl groups, polycyclic groups, aryl groups, polyaryl groups, substituted aryl groups, heterocyclic groups, and substituted heterocyclic groups. Linking groups may also comprise poly ethoxy aminoacids such as AEA ((2-amino) ethoxy acetic acid) or a preferred linking group AEEA ([2-(2-amino) ethoxy)]ethoxy acetic acid).

Blood Components: Blood components may be either fixed or mobile. Fixed blood components are non-mobile blood components and include tissues, membrane receptors, interstitial proteins, fibrin proteins, collagens, platelets, endothelial cells, epithelial cells and their associated membrane and membraneous receptors, somatic body cells, skeletal and smooth muscle cells, neuronal components, osteocytes and osteoclasts and all body tissues especially those associated with the circulatory and lymphatic systems. Mobile blood components are blood components that do not have a fixed situs for any extended period of time, generally not exceeding 5, more usually one minute. These blood components are not membrane-associated and are present in the blood for extended periods of time and are present in a minimum concentration of at least 0.1 µg/ml. Mobile blood components include serum albumin. transferrin, ferritin and immunoglobulins such as IgM and IgG. The half-life of mobile blood components is at least about 12 hours.

Protective Groups: Protective groups are chemical moieties utilized to protect peptide derivatives from reacting with themselves. Various protective groups are disclosed herein and in U.S. Pat. No. 5,493,007 which is hereby incorporated by reference. Such protective groups include acetyl, fluorenylmethyloxycarbonyl (FMOC), t-butyloxycarbonyl (BOC), benzyloxycarbonyl (CBZ), and the like. The specific protected amino acids are depicted in Table 1.

TABLE 1

NATURAL AMINO ACIDS AND THEIR ABBREVIATIONS

| Name | 3-Letter Abbreviation | 1-Letter Abbreviation | Protected Amino Acids |
|---|---|---|---|
| Alanine | Ala | A | Fmoc-Ala-OH |
| Arginine | Arg | R | Fmoc-Arg(Pbf)-OH |
| Asparagine | Asn | N | Fmoc-Asn(Trt)-OH |
| Aspartic acid | Asp | D | Asp(tBu)-OH |
| Cysteine | Cys | C | Fmoc-Cys(Trt) |
| Glutamic acid | Glu | E | Fmoc-Glu(tBu)-OH |
| Glutamine | Gln | Q | Fmoc-Gln(Trt)-OH |
| Glycine | Gly | G | Fmoc-Gly-OH |
| Histidine | His | H | Fmoc-His(Trt)-OH |
| Isoleucine | Ile | I | Fmoc-Ile-OH |
| Leucine | Leu | L | Fmoc-Leu-OH |
| Lysine | Lys | K | Fmoc-Lys(Mtt)-OH |
| Methionine | Met | M | Fmoc-Met-OH |
| Phenylalanine | Phe | F | Fmoc-Phe-OH |
| Proline | Pro | P | Fmoc-Pro-OH |
| Serine | Ser | S | Fmoc-Ser(tBu)-OH |
| Threonine | Thr | T | Fmoc-Thr(tBu)-OH |
| Tryptophan | Trp | W | Fmoc-Trp(Boc)-OH |
| Tyrosine | Tyr | Y | Boc-Tyr(tBu)-OH |
| Valine | Val | V | Fmoc-Val-OH |

Sensitive Functional Groups—A sensitive functional group is a group of atoms that represents a potential reaction site on an ITP peptide. If present, a sensitive functional group may be chosen as the attachment point for the linker-reactive group modification. Sensitive functional groups include but are not limited to carboxyl, amino, thiol, and hydroxyl groups.

Modified Peptides—A modified ITP is a peptide that has been modified by attaching a reactive group, and is capable of forming a peptidase stabilized peptide through conjugation to blood components. The reactive group may be attached to the therapeutic peptide either via a linking group, or optionally without using a linking group. It is also contemplated that one or more additional amino acids may be added to the therapeutic peptide to facilitage the attachment of the reactive group. Modified peptides may be administered in vivo such that conjugation with blood components occurs in vivo, or they may be first conjugated to blood components in vitro and the resulting peptidase stabalized peptide (as defined below) administered in vivo. The terms "modified therapeutic peptide" and "modified peptide" may be used interchangeably in this application.

Peptidase Stabilized ITP—A peptidase stabilized ITP is a modified peptide that has been conjugated to a blood component via a covalent bond formed between the reactive group of the modified peptide and the functionalities of the blood component with or without a linking group. Peptidase stabilized peptides are more stable in the presence of peptidases in vivo than a non-stabilized peptide. A peptidase stabilized therapeutic peptide generally has an increased half life of at least 10-50% as compared to a non stabalize peptide of identical sequence. Peptidase stability is determined by comparing the half life of the unmodified ITP in serum or blood to the half life of a modified counterpart therapeutic peptide in serum or blood. Half life is determined by sampling the serum or blood after administration of the modified and non-modified peptides and determining the activity of the peptide. In addition to determining the activity, the length of the ITP may also be measured by HPLC and Mass Spectrometry.

DETAILED DESCRIPTION OF THE INVENTION

Taking into account these definitions the focus of this invention is to modify insulinotropic peptides to improve bio-availability, extend half-life and distribution through selective conjugation onto a protein carrier but without modifying their remarkable therapeutic properties. The carrier of choice (but not limited to) for this invention would be albumin conjugated through its free thiol by a insulinotropic peptide derivatized with a maleimide moiety.

1. Insulinotropic Peptides

A. GLP-1 and its Derivatives

The hormone glucagon is known to be synthesized as a high molecular weight precursor molecule which is subsequently proteolytically cleaved into three peptides: glucagon, glucagon-like peptide 1 (GLP-1), and glucagon-like peptide 2 (GLP-2). GLP-1 has 37 amino acids in its unprocessed form as shown in SEQ ID NO: 1. Unprocessed GLP-1 is essentially unable to mediate the induction of insulin biosynthesis. The unprocessed GLP-1 peptide is, however, naturally converted to a 31-amino acid long peptide (7-37 peptide) having amino acids 7-37 of GLP-1 ("GLP-1(7-37)") SEQ ID NO:2. GLP (7-37) can also undergo additional processing by proteolytic removal of the C-terminal glycine to produce GLP-1(7-36) which also exists predominantly with the C-terminal residue, arginine. In amidated form as arginineamide, GLP-1(7-36) amide. This processing occurs in the intestine and to a much lesser extent in the pancreas, and results in a polypeptide with the insulinotropic ac of GLP-1(7-37).

A compound is said to have an "insulinotropic activity" if it is able to stimulate, or cause the stimulation of, the synthesis or expression of the hormone insulin. The hormonal activity of GLP4(7-37) and GLP-1(7-36) appear to be specific for the pancreatic beta cells where it appears to induce the biosynthesis of insulin. The glucagon-like-peptide hormone of the invention is useful in the study of the pathogenesis of maturity onset diabetes mellitus, a condition characterized by hyperglycemia in which the dynamics of insulin secretion are abnormal. Moreover, the glucagon-like peptide is useful in the therapy and treatment of this disease, and in the therapy and treatment of hyperglycemia.

Peptide moieties (fragments) chosen from the determined amino acid sequence of human GLP-1 constitute the starting point in the development comprising the present invention. The interchangeable terms "peptide fragment" and "peptide moiety" are meant to include both synthetic and naturally occurring amino acid sequences derivable from a naturally occurring amino acid sequence.

The amino acid sequence for GLP-1 has been reported by several researchers (Lopez, L. C., et al., Proc. Natl. Acad. Sci., USA 80:548-5489 (1983); Bell, G. I., et al., Nature 302:716-718 (1983); Heinrich, G., et al., Endocrinol. 115:2176-2181 (1984)). The structure of the preproglucagon mRNA and its corresponding amino acid sequence is well known. The proteolytic processing of the precursor gene product proglucagon, into glucagon and the two insulinotropic peptides has been characterized. As used herein, the notation of GLP-1(1-37) refers to a GL-1 polypeptide having all amino adds from 1 (N-terminus) through 37 (C-terminus). Similarly, GLP-1(7-37) refers to a GLP-1 polypeptide having all amino acids from 7 (N-terminus) through 37 (C-terminus). Similarly, GLP-1(7-36) refers to a GLP-1 polypeptide having all amino acids from number 7 (N-terminus) through number 36 (C-terminus).

In one embodiment, GLP-1(7-36) and its peptide fragments are synthesized by conventional means as detailed below, such as by the well-known solid-phase peptide synthesis described by Merrifield, J. M. (Chem. Soc. 85:2149 (1962)), and Stewart and Young (Solid Phase Peptide Synthesis (Freeman, San Francisco. 1969). pages 27-66). which are incorporated by reference herein. However, it is also possible to obtain fragments of the proglucagon polypeptide, or of GLP-1, by fragmenting the naturally occurring amino acid sequence, using, for example, a proteolytic enzyme. Further, it is possible to obtain the desired fragments of the proglucagon peptide or of GLP-1 through the use of recombinant DNA technology, as disclosed by Maniatis, T., et al., Molecular Biology: A Laboratory Manual, Cold Spring Harbor, N.Y. (1982), which is hereby incorporated by reference.

The present invention includes peptides which are derivable from GLP-1 such as GLP-1(1-37) and GLP-1(7-36). A peptide is said to be "derivable from a naturally occurring amino acid sequence" if it can be obtained by fragmenting a naturally occurring sequence, or if it can be synthesized based upon a knowledge of the sequence of the naturally occurring amino acid sequence or of the genetic material (DNA or RNA) which encodes this sequence.

Included within the scope of the present invention are those molecules which are said to be "derivatives" of GLP-1 such as GLP-1(1-37) and especially GLP-1(7-36). Such a "derivative" has the following characteristics: (1) it shares substantial homology with GLP-1 or a similarly sized fragment of GLP-1; (2) it is capable of functioning as an insulinotropic hormone and (3) using at last one of the assays provided herein, the derivative has either (i) an insulinotropic activity which exceeds the insulinotropic activity of either GLP-1, or, more preferably, (ii) an insulinotropic activity which can be detected even when the derivative is present at a concentration of $10^{-10}$ M, or, most preferably, (iii) an insulinotropic activity which can be detected even when the derivative is present at a concentration of $10^{-11}$ M.

A derivative of GLP-1 is said to share "substantial homology" with GLP-1 if the amino acid sequences of the derivative is at least 80%, and more preferably at least 90%, and most preferably at least 95%, the same as that of GLP-1(1-37).

The derivatives of the present invention include GLP-1 fragments which, in addition to containing a sequence that is substantially homologous to that of a naturally occurring GLP-1 peptide may contain one or more additional amino acids at their amino and/or their carboxy termini. Thus, the invention pertains to polypeptide fragments of GLP-1 that may contain one or more amino acids that may not be present in a naturally occurring GLP-1 sequence provided that such polypeptides have an insulinotropic activity which exceeds that of GLP-1. The additional amino acids may be D-amino acids or L-amino acids or combinations thereof.

The invention also includes GLP-1 fragments which, although containing a sequence that is substantially homologous to that of a naturally occurring GLP-1 peptide may lack one or more additional amino acids at their amino and/or their carboxy termini that are naturally found on a GLP-1 peptide. Thus, the invention pertains to polypeptide fragments of GLP-1 that may lack one or more amino acids that are normally present in a naturally occurring GLP-1 sequence provided that such polypeptides have an insulinotropic activity which exceeds that of GLP-1.

The invention also encompasses the obvious or trivial variants of the above-described fragments which have inconsequential amino acid substitutions (and thus have amino acid sequences which differ from that of the natural sequence) provided that such variants have an insulinotropic activity which is substantially identical to that of the above-described GLP-1 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

In addition to those GLP-1 derivatives with insulinotropic activity, GLP-1 derivatives which stimulate glucose uptake by cells but do not stimulate insulin expression or secretion are within the scope of this invention. Such GLP-1 derivatives are described in U.S. Pat. No. 5,574,008.

GLP-1 derivatives which stimulate glucose uptake by cells but do not stimulate insulin expression or secretion which find use in the invention include: $R_1$-Ser-Tyr-Leu-Glu-Gly-Gln-Ala-Ala-Lys-Glu-Phe-Ile-Ala-Trp-Leu-Val-Xaa-Gly-Arg-$R_2$ (SEQ ID NO:3) wherein $R_1$ is selected from a) $H_2N$; b) $H_2N$-Ser; c) $H_2N$-Val-Ser; d) $H_2N$-Asp-Val-Ser; e) $H_2N$-Ser-Asp-Val-Ser (SEQ ID NO:4); f) $H_2N$-Thr-Ser-Asp-Val-Ser (SEQ ID NO:5); g) $H_2N$-Phe-Thr-Ser-Asp-Val-Ser (SEQ ID NO:6); h) $H_2N$-Thr-Phe-Thr-Ser-Asp-Val-Ser (SEQ ID NO:7); i) $H_2N$-Gly-Thr-Phe-Thr-Ser-Asp-Val-Ser (SEQ ID NO:8); j) $H_2N$-Glu-Gly-Thr-Phe-Thr-Ser-Asp-Val-Ser (SEQ ID NO:9); or, k) $H_2N$-Ala-Glu-Gly-Thr-Phe-Thr-Ser-Asp-Val-Ser (SEQ ID NO:10). In the peptide, X is selected from Lys or Arg and $R_2$ is selected from $NH_2$, OH, Gly-$NH_2$, or Gly-OH. These peptides are C-terminal GLP-1 fragments which do not have insulinotropic activity but which are nonetheless useful for treating diabetes and hyperglycemic conditions as descried in U.S. Pat. No. 5,574,008.

B. Exendin 3 and Exendin 4 Peptides

Exendin 3 and Exendin 4 are 39 amino acid peptides (differing at residues 2 and 3) which are approximately 53% homologous to GLP-1 and find use as insulinotropic agents.

The Exendin-3 [SEQ ID No:11] sequence is HSDGTFTSDLSKQMEEEAVRLFIEWLKNGG PSSGAPPPS and The Exendin-4 [SEQ ID No:12] sequence is HGEGTFTSDLSKQMEEEAVRLFIEWLKNGG PSSGAPPPS.

The invention also encompasses the insulinotropic fragments of exendin-4 comprising the amino acid sequences: Exendin-4(1-31) [SEQ ID No:13] HGEGTFTSDLSKQMEEAVR LFIEWLKNGGPY and Exendin-4 (1-31) [SEQ ID No:14] HGEGTFTSDLSKQMEEEAVR-LFIEWLKNGGY.

The invention also encompasses the inhibitory fragment of exendin-4 comprising the amino acid sequence:

Exendin-4(9-39) [SEQ ID No:15] DLSKQMEEEAVR-LFIEWLKNGGPSSGAPPPS

Other insulinotropic peptides as presented in the Examples are shown as SEQ ID NO:16-22.

The present invention includes peptides which are derivable from the naturally occurring exendin 3 and exendin 4 peptides. A peptide is said to be "derivable from a naturally occurring amino acid sequence" if it can be obtained by fragmenting a naturally occurring sequence, or if it can be synthesized based upon a knowledge of the sequence of the naturally occurring amino acid sequence or of the genetic material (DNA or RNA) which encodes this sequence.

Included within the scope of the present invention are those molecules which are said to be "derivatives" of exendin 3 and exendin 4. Such a "derivative" has the following characteristics: (1) it shares substantial homology with exendin 3 or exendin 4 or a similarly sized fragment of exendin 3 or exendin 4; (2) it is capable of functioning as an insulinotropic hormone and (3) using at least one of the assays provided herein, the derivative has either (i) an insulinotropic activity which exceeds the insulinotropic activity of either exendin 3 or exendin 4, or, more preferably, (ii) an insulinotropic activity which can be detected even when the derivative is present at a concentration of $10^{-10}$ M, or, most preferably, (iii) an insulinotropic activity which can be detected even when the derivative is present at a concentration of $10^{-11}$ M.

A derivative of exendin 3 and exendin 4 is said to share "substantial homology" with exendin 3 and exendin 4 if the amino acid sequences of the derivative is at least 80%, and more preferably at least 90%, and most preferably at least 95%, the same as that of either exendin 3 or 4 or a fragment of exendin 3 or 4 having the same number of amino acid residues as the derivative.

The derivatives of the present invention include exendin 3 or exendin 4 fragments which, in addition to containing a sequence that is substantially homologous to that of a naturally occurring exendin 3 or exendin 4 peptide may contain one or more additional amino acids at their amino and/or their carboxy termini. Thus, the invention pertains to polypeptide fragments of exendin 3 or exendin 4 that may contain one or more amino acids that may not be present in a naturally occurring exendin 3 or exendin 4 sequences provided that such polypeptides have an insulinotropic activity which exceeds that of exendin 3 or exendin 4.

Similarly, the invention includes exendin 3 or exendin 4 fragments which, although containing a sequence that is substantially homologous to that of a naturally occurring exendin 3 or exendin 4 peptide may lack one or more additional amino adds at their amino and/or their carboxy termini that are naturally found on a exendin 3 or exendin 4 peptide. Thus, the invention pertains to polypeptide fragments of exendin 3 or exendin 4 that may lack one or more amino acids that are normally present in a naturally occurring exendin 3 or exendin 4 sequence provided that such polypeptides have an insulinotropic activity which exceeds that of exendin 3 or exendin 4.

The invention also encompasses the obvious or trivial variants of the above-described fragments which have inconsequential amino acid substitutions (and thus have amino acid sequences which differ from that of the natural sequence) provided that such variants have an insulinotropic activity which is substantially identical to that of the above-described exendin 3 or exendin 4 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

2. Modified Insulinotropic Peptides

This invention relates to modified insulinotropic peptides and their derivatives. The modified insulinotropic peptides of the invention include reactive groups which can react with available reactive functionalities on blood components to form covalent bonds. The invention also relates to such modifications, such combinations with blood components and methods for their use. These methods include extending the effective therapeutic in vivo half life of the modified insulinotropic peptides.

To form covalent bonds with the functional group on a protein, one may use as a chemically reactive group (reactive entity) a wide variety of active carboxyl groups, particularly esters, where the hydroxyl moiety is physiologically acceptable at the levels required to modify the insulinotropic peptides. While a number of different hydroxyl groups may be employed in these linking agents, the most convenient would be N-hydroxysuccinimide (NHS), N-hydroxy-sulfosuccinimide (sulfo-NHS), maleimide-benzoyl-succinimide (MBS), gamma-maleimido-butyloxy succinimide ester (GMBS) and maleimidopropionic acid (MPA).

Primary amines are the principal targets for NHS esters as diagramed in the schematic below." Accessible α-amine groups present on the N-termini of proteins react with NHS esters. However, α-amino groups on a protein may not be desirable or available for the NHS coupling. While five amino acids have nitrogen in their side chains, only the ε-amine of lysine reacts significantly with NHS esters. An amide bond is formed when the NHS ester conjugation reaction reacts with primary amines releasing N-hydroxysuccinimide as demonstrated in the schematic below. These succinimide containing reactive groups are herein referred to as succinimidyl groups.

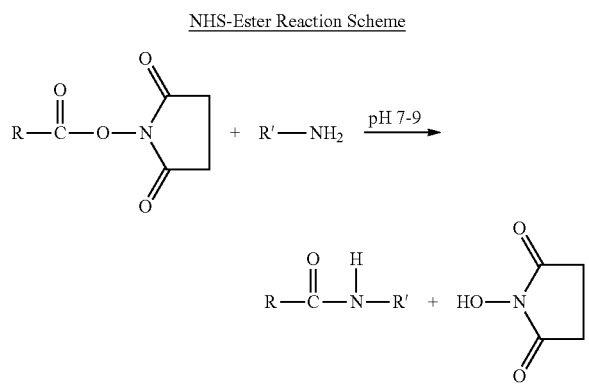

NHS-Ester Reaction Scheme

In the preferred embodiments of this invention, the functional group on the protein will be a thiol group and the chemically reactive group will be a maleimido-containing group such as (GMBA or MPA). GMBA stands for gamma-maleimide-butrylamide. Such maleimide containing groups are referred to herein as maleido groups.

The maleimido group is most selective for sulfhydryl groups on peptides when the pH of the reaction mixture is kept between 6.5 and 7.4. At pH 7.0, the rate of reaction of maleimido groups with sulfhydryls is 1000-fold faster than with amines. A stable thioether linkage between the maleimido group and the sulfhydryl is formed which cannot be cleaved under physiological conditions.

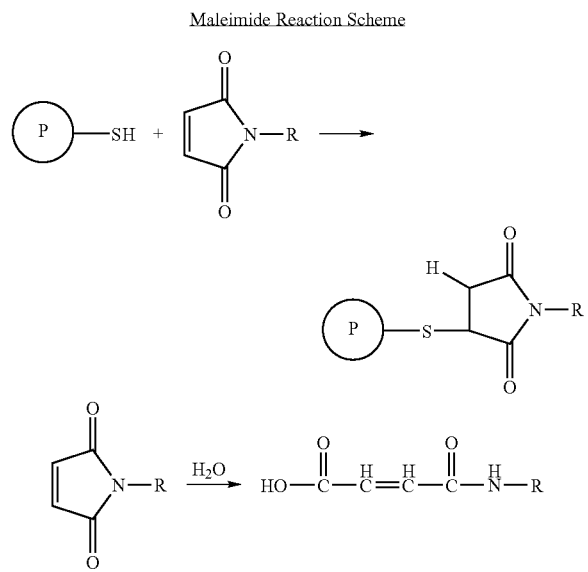

Maleimide Reaction Scheme

The insulinotropic peptides and peptide derivatives of the invention may be modified for specific labeling and non-specific labeling of blood components.

A. Specific Labeling

Preferably, the modified insulinotropic peptides (ITP) of this invention are designed to specifically react with thiol groups on mobile blood proteins. Such reaction is preferably established by covalent bonding of a therapeutic peptide modified with a maleimide link (e.g. prepared from GMBS, MPA or other maleimides) to a thiol group on a mobile blood protein such as serum albumium or IgG.

Under certain circumstances, specific labeling with maleimides offers several advantages over non-specific labeling of mobile proteins with groups such as NHS and sulfo-NHS. Thiol groups are less abundant in vivo than amino groups. Therefore, the maleimide derivatives of this invention will covalently bond to fewer proteins. For example, in albumin (the most abundant blood protein) there is only a single thiol group. Thus, ITP-maleimide-albumin conjugates will tend to comprise approximately a 1:1 molar ratio of IP to albumin. In addition to albumin. IgG molecules (class II) also have free thiols. Since IgG molecules and serum albumin make up the majority of the soluble protein in blood they also make up the majority of the free thiol groups in blood that are available to covalently bond to maleimide-modified ITPs.

Further, even among free thiol-containing blood proteins, specific labeling with maleimides leads to the preferential formation of ITP-maleimide-albumin conjugates, due to the unique characteristics of albumin itself. The single free thiol group of albumin, highly conserved among species, is located at amino acid residue 34 ($Cys^{34}$). It has been demonstrated recently that the $Cys^{34}$ of albumin has increased reactivity relative to free thiols on other free thiol-containing proteins. This is due in part to the very low pK value of 5.5 for the $Cys^{34}$ of albumin. This is much lower than typical pK values for cysteines residues in general, which are typically about 8. Due to this low pK, under normal physiological conditions $Cys^{34}$ of albumin is predominantly in the ionized form, which dramatically increases its reactivity, as reported in. In addition to the low pK value of $Cys^{34}$, another factor which enhances the reactivity of $Cys^{34}$ is its location, which is in a crevice close to the surface of one loop of region V of albumin. This location makes $Cys^{34}$ very available to ligands of all kinds, and is an important factor in $Cys^{34}$'s biological role as free radical trap and free thiol scavenger. These properties make $Cys^{34}$ highly reactive with ITP-maleimides, and the reaction rate acceleration can be as much as 1000-fold relative to rates of reaction of TP-maleimides with other free-thiol containing proteins.

Another advantage of ITP-maleimide-albumin conjugates is the reproducibility associated with the 1:1 loading of peptide to albumin specifically at $Cys^{34}$. Other techniques, such as glutaraldehyde, DCC, EDC and other chemical activations of, for example, free amines lack this selectivity. For example, albumin contains 52 lysine residues, 25-30 of which are located on the surface of albumin and accessible for conjugation. Activating these lysine residues, or alternatively modifying peptides to couple through these lysine residues, results in a heterogenous population of conjugates. Even if 1:1 molar ratios of peptide to albumin are employed, the yield will consist of multiple conjugation products, some containing 0, 1, 2 or more peptides per albumin, and each having peptides randomly coupled at any one of the 25-30 available lysine sites. Given the numerous combinations possible, characterization of the exact composition and nature of each batch becomes difficult, and batch-to-batch reproducibility is all but impossible, making such conjugates less desirable as a therapeutic. Additionally, while it would seem that conjugation through lysine residues of albumin would at least have the advantage of delivering more therapeutic agent per albumin molecule, studies have shown that a 1:1 ratio of therapeutic agent to albumin is preferred. In an article by Stehle, et al., "The Loading Rate Determines Tumor Targeting Properties of Methotrexate-Albumin Conjugates in Rats," *Anti-Cancer Drugs*, Vol. 8, pp. 677-685 (1997), incorporated herein in its entirety, the authors report that a 1:1 ratio of the anti-cancer methotrexate to albumin conjugated via glutaraldehyde gave the most promising results. These conjugates were taken up by tumor cells, whereas conjugates bearing 5:1 to 20:1 methotrexate molecules had altered HPLC profiles and were quickly taken up by the liver in vivo. It is postulated that at these higher ratios, conformational changes to albumin diminish its effectiveness as a therapeutic carrier.

Through controlled administration of maleimide-ITPs in vivo, one can control the specific labeling of albumin and IgG in vivo. In typical administrations, 80-90% of the administered maleimide-ITPs will label albumin and less than 5% will label IgG. Trace labeling of free thiols such as glutathione will also occur. Such specific labeling is preferred for in vivo use as it permits an accurate calculation of the estimated half-life of the administered agent.

In addition to providing controlled specific in vivo labeling, maleimide-TPs can provide specific labeling of serum albumin and IgG ex vivo. Such ex vivo labeling involves the addition of maleimide-ITPs to blood, serum or saline solution containing serum albumin and/or IgG. Once modified ex vivo with maleimide-TPs, the blood, serum or saline solution can be readministered to the blood for in vivo treatment.

In contrast to NHS-peptides, maleimide-ITPs are generally quite stable in the presence of aqueous solutions and in the presence of free amines. Since maleimide-ITPs will only react with free thiols, protective groups are generally not necessary to prevent the maleimide-ITPs from reacting with itself. In addition, the increased stability of the peptide permits the use of further purification steps such as HPLC to prepare highly purified products suitable for in vivo use. Lastly, the increased chemical stability provides a product with a longer shelf life.

B. Non-Specific Labeling

The ITPs of the invention may also be modified for non-specific labeling of blood components. Bonds to amino groups will generally be employed, particularly with the formation of amide bonds for non-specific labeling. To form such bonds, one may use as a chemically reactive group coupled to the ITP a wide variety of active carboxyl groups, particularly esters, where the hydroxyl moiety is physiologically acceptable at the levels required. While a number of different hydroxyl groups may be employed in these linking agents, the most convenient would be N-hydroxysuccinimide (NHS) and N-hydroxy-sulfosuccinimide (sulfo-NHS).

Other linking agents which may be utilized are described in U.S. Pat. No. 5,612,034, which is hereby incorporated herein.

The various sites with which the chemically reactive groups of the non-specific ITPs may react in vivo include cells, particularly red blood cells (erythrocytes) and platelets, and proteins, such as immunoglobulins, including IgG and IgM, serum albumin, ferritin, steroid binding proteins, transferrin, thyroxin binding protein, α-2-macroglobulin, and the like. Those receptors with which the derivatized ITPs react, which are not long-lived, will generally be eliminated from the human host within about three days. The proteins indicated above (including the proteins of the cells) will remain in the bloodstream at least three days, and may remain five days or more (usually not exceeding 60 days, more usually not exceeding 30 days) particularly as to the half life, based on the concentration in the blood.

For the most part, reaction will be with mobile components in the blood, particularly blood proteins and cells, more particularly blood proteins and erythrocytes. By "mobile" is intended that the component does not have a fixed situs for any extended period of time, generally not exceeding 5 minutes, more usually one minute, although some of the blood components may be relatively stationary for extended periods of time. Initially, there will be a relatively heterogeneous population of labeled proteins and cells. However, for the most part, the population within a few days after administration will vary substantially from the initial population, depending upon the half-life of the labeled proteins in the blood stream. Therefore, usually within about three days or more, IgG will become the predominant labeled protein in the blood stream.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

The desired conjugates of non-specific ITPs to blood components may be prepared in vivo by administration of the ITPs directly to the patient, which may be a human or other mammal. The administration may be done in the form of a bolus or introduced slowly over time by infusion using metered flow or the like.

If desired, the subject conjugates may also be prepared ex vivo by combining blood with derivatized ITPs of the present invention, allowing covalent bonding of the modified ITPs to reactive functionalities on blood components and then returning or administering the conjugated blood to the host. Moreover, the above may also be accomplished by first purifying an individual blood component or limited number of components, such as red blood cells, immunoglobulins, serum albumin, or the like, and combining the component or components ex vivo with the chemically reactive ITPs. The labeled blood or blood component may then be returned to the host to provide in vivo the subject therapeutically effective conjugates. The blood also may be treated to prevent coagulation during handling ex vivo.

3. Synthesis of Modified ITPs

A. ITP Synthesis

ITP fragments may be synthesized by standard methods of solid phase peptide chemistry known to those of ordinary skill in the art. For example, ITP fragments may be synthesized by solid phase chemistry techniques following the procedures described by Steward and Young (Steward, J. M. and Young, J. D., Solid Phase Peptide Synthesis, 2nd Ed., Pierce Chemical Company, Rockford, Ill., (1984) using an Applied Biosystem synthesizer. Similarly, multiple fragments may be synthesized then linked together to form larger fragments. These synthetic peptide fragments can also be made with amino acid substitutions at specific locations.

For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, Vol. 1, Acacemic Press (New York). In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a property protected dipeptide to form, after deprotection, a pentapeptide.

A particularly preferred method of preparing compounds of the present invention involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenyl-methyloxycarbonyl (Fmoc) protecting group is particularly preferred for the synthesis of ITP fragments. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxycarbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of α-C-terminal carboxy peptides is 4-hydroxytethylphenoxymethyl-copoly(styrene-1% divinylbenzene). The preferred solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyolohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours at a temperature of between 10° and 50° C. in a solvent such as dichloromethane or DMF.

When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. The preferred method for coupling to the deprotected 4-(2',4'-dimethoxyphenyl-Fmoc-aminomethyl)phenoxy-acetamidoethyl resin is O-benzotriazol-1-yl-N,N,N',N'-tetramethyluroniumhexafluoro-phosphate (HBTU, 1 equiv.) and 1-hydroxybenzotriazole (HOBT, 1 equiv.) in DMF. The coupling of successive protected amino acids can be carried out in an automatic polypeptide synthesizer as is well known in the art. In a preferred embodiment, the α-N-terminal amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N, N',N'-tetramethyluroniumhexafluoro-phosphate (HBTU, 1 equiv.) and 1-hydroxybenzotriazole (HOBT, 1 equiv.).

At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above. The fully deprotected peptide is purified by a sequence of chromatographic steps employing any or all of the following types: ion exchange on a weakly basic resin (acetate form); hydrophobic adsorption chromatography on underivitized polystyrene-divinylbenzene (for example. Amberlite XAD); silica gel adsorption chromatography; ion exchange chromatography on carboxymethylcellulose; partition chromatography, e.g. on Sephadex G-25. LH-20 or countercurrent distribution; high performance liquid chromatography (HPLC), especially reverse-phase HPLC on octyl- or octadecylsilyl-silica bonded phase column packing.

Molecular weights of these ITPs are determined using Fast Atom Bombardment (FAB) Mass Spectroscopy.

The ITPs of the invention may be synthesized with N- and C-terminal protecting groups for use as pro-drugs.

1. N-Terminal Protective Groups

As discussed above, the term "N-protecting group" refers to those groups intended to protect the α-N-terminal of an amino acid or peptide or to otherwise protect the amino group of an amino acid or peptide against undesirable reactions during synthetic procedures. Commonly used N-protecting groups are disclosed in Greene, "Protective Groups in Organic Synthesis," (John Wiley & Sons, New York (1981)), which is hereby incorporated by reference. Additionally, protecting groups can be used as pro-drugs which are readily cleaved in vivo, for example, by enzymatic hydrolysis, to release the biologically active parent. α-N-protecting groups comprise loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-triloroethoxycarbonyl, phenoxycarbonyl, 4-nitrophenoxycarbonyl, fluorenyl-9-methoxycarbonyl, cyclopentyloxycarbonyl, adamantyloxycarbonyl, cydohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like.

2. Carboxy Protective Groups

As discussed above, the term "carboxy protecting group" refers to a carboxylic acid protecting ester or amide group employed to block or protect the carboxylic acid functionary while the reactions involving other functional sites of the compound are performed. Carboxy protecting groups are disclosed in Greene, "Protective Groups in Organic Synthesis" pp. 152-186 (1981), which is hereby incorporated by reference. Additionally, a carboxy protecting group can be used as a pro-drug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are $C_1$-$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyioxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cydoalkyloxycarbonylalkyl such as methoxycarbonylmethyl, cyclohexyloxycarbonylmethyl, 1-ethoxycarbonyl-1-ethyl and the like; alkoxycarbonyloxyalkyl or cycloalkyloxycarbonyloxyalkyl such as methoxycarbonyloxymethyl t-butyloxycarbonyloxymethyl, 1-ethoxycarbonyloxy-1-ethyl, 1-clohexyloxycarbonyloxy-1-ethyl and the like; aryloxycarbonyloxyalkyl such as 2-(phenoxycarbonyloxy)ethyl, 2-(5-indanyloxycarbonytoxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like.

Representative amide carboxy protecting groups are aminocarbonyl and loweralkylaminocarbonyl groups.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octal ester, cyclohexyl ester, phenylethyl ester and the like or an alkanoyloxyalkyl, cycloalkanoyloxyalkyl, aroyloxyalkyl or an arylalkylcarbonyloxyalkyl ester. Preferred amide carboxy protecting groups are loweralkylaminocarbonyl groups. For example, aspartic acid may be protected at the α-C-terminal by an acid labile group (e.g. t-butyl) and protected at the β-C-terminal by a hydrogenation labile group (e.g. benzyl) then deprotected selectively during synthesis.

B. Modification of ITPs

The manner of producing the modified ITPs of the present invention will vary widely, depending upon the nature of the various elements comprising the ITP. The synthetic procedures will be selected so as to be simple, provide for high yields, and allow for a highly purified product. Normally, the chemically reactive group will be created at the last stage of the synthesis, for example, with a carboxyl group, esterification to form an active ester. Specific methods for the production of modified ITPs of the present invention are described below.

Each ITP selected to undergo the modification with a linker and a reactive agent is modified according to the following criteria: if a carboxylic group, not critical for the retention of pharmacological activity is available on the original ITP and no other reactive functionality is present on the ITP, then the carboxylic acid is chosen as attachment point for the linker-reactive entity modification. If no carboxylic acids are available, then other functionalities not critical for the retention of pharmacological activity are selected as an attachment point for the linker-reactive entity modification. If several functionalities are available on a an ITP, a combination of protecting groups will be used in such a way that after addition of the linker/reactive entity and deprotection of all the protected functional groups, retention of pharmacological activity is still obtained. If no reactive functionalities are available on the ITP, synthetic efforts will allow for a modification of the original ITP in such a way that retention of biological activity and retention of receptor or target specificity is obtained.

The chemically reactive entity is placed at a site so that when the ITP is bonded to the blood component, the ITP retains a substantial proportion of the unmodified ITP's activity.

Even more specifically, each ITP selected to undergo the derivatization with a linker and a reactive entity will be modified according to the following criteria: if a terminal carboxylic group is available on the therapeutic peptide and is not critical for the retention of pharmacological activity, and no other sensitive functional group is present on the ITP, then the carboxylic acid will be chosen as attachment point for the linker-reactive entity modification. If the terminal carboxylic group is involved in pharmacological activity, or if no carboxylic acids are available, then any other sensitive functional group not critical for the retention of pharmacological activity will be selected as the attachment point for the linker-reactive entity modification. If several sensitive functional groups are available on a ITP, a combination of protecting groups will be used in such a way that after addition of the linker/reactive entity and deprotection of all the protected sensitive functional groups, retention of pharmacological activity is still obtained. If no sensitive functional groups are available on the therapeutic peptide, synthetic efforts will allow for a modification of the original peptide in such a way that retention of biological activity and retention of receptor or target specificity is obtained. In this case the modification will occur at the opposite end of the peptide.

An NHS derivative may be synthesized from a carboxylic acid in absence of other sensitive functional groups in the therapeutic peptide. Specifically, such a therapeutic peptide is reacted with N-hydroxysuccinimide in anhydrous $CH_2 Cl_2$ and EDC, and the product is purified by chromatography or recrystallized from the appropriate solvent system to give the NHS derivative.

Alternatively, an NHS derivative may be synthesized from a ITP that contains an amino and/or thiol group and a carboxylic acid. When a free amino or thiol group is present in the molecule, it is preferable to protect these sensitive functional groups prior to perform the addition of the NHS derivative. For instance, if the molecule contains a free amino group, a transformation of the amine into a Fmoc or preferably into a tBoc protected amine is necessary prior to perform the chemistry described above. The amine functionality will not be deprotected after preparation of the NHS derivative. Therefore this method applies only to a compound whose amine group is not required to be freed to induce a pharmacological desired effect. In addition, an NHS derivative may be synthesized from a therapeutic peptide containing an amino or a thiol group and no carboxylic acid. When the selected molecule contains no carboxylic acid, an array of bifunctional linkers can be used to convert the molecule into a reactive NHS derivative. For instance, ethylene glycol-bis (succinimydylsuccinate) (EGS) and triethylamine dissolved in DMF and added to the free amino containing molecule (with a ratio of 10:1 in favor of EGS) will produce the mono NHS derivative. To produce an NHS derivative from a thiol derivatized molecule, one can use N-[-maleimidobutyryloxy] succinimide ester (GMBS) and triethylamine in DMF. The maleimido group will react with the free thiol and the NHS derivative will be purified from the reaction mixture by chromatography on silica or by HPLC.

An NHS derivative may also be synthesized from a ITP containing multiple sensitive functional groups. Each case will have to be analyzed and solved in a different manner. However, thanks to the large array of protecting groups and bifunctional linkers that are commercially available, this invention is applicable to any therapeutic peptide with preferably one chemical step only to derivatize the ITP or two steps by first protecting a sensitive group or three steps (protection, activation and deprotection). Under exceptional circumstances only, would one require to use multiple steps (beyond three steps) synthesis to transform a therapeutic peptide into an active NHS or maleimide derivative.

A maleimide derivative may also be synthesized from an ITP containing a free amino group and a free carboxylic acid. To produce a maleimide derivative from a amino derivatized molecule, one can use N-[-maleimidobutyryloxy]succinimide ester (GMBS) and triethylamine in DMF. The succinimide ester group will react with the free amino and the maleimide derivative will be purified from the reaction mixture by crystallization or by chromatography on silica or by HPLC.

Finally, a maleimide derivative may be synthesized from a therapeutic peptide containing multiple other sensitive functional groups and no free carboxylic acids. When the selected molecule contains no carboxylic acid, an array of bifunctional crosslinking reagents can be used to convert the molecule into a reactive NHS derivative. For instance maleimidopropionic acid (MPA) can be coupled to the free amine to produce a maleimide derivative through reaction of the free amine with the carboxylic group of MPA using HBTU/HOBt/DIEA activation in DMF.

Many other commercially available heterobifunctional crosslinking reagents can alternatively be used when needed. A large number of bifunctional compounds are available for linking to entities. Illustrative reagents include: azidobenzoyl hydrazide, N-[4-p-azidosalicylamino)butyl]-3'-[2'-pyridyldithio)propionamide), bis-sulfosuccinimidyl suberate, dimethyl adipimidate, disuccinimidyl tartrate, N-γ-maleimidobutnyloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl 4-[N-maleimidomethyl]cyclohexane-1-carboxylate, 4. Uses of the Modified ITPs The modified ITPs of the invention find multiple uses including use as a treatment for diabetes, a sedative, a treatment of nervous system disorders, use to induce an anxiolytic effect on the CNS, use to activate the CNS, use for post surgery treatment and as a treatment for insulin resistance.

A. Diabetes Treatments

The modified ITPs of the invention generally will normalize hyperglycemia through glucose-dependent, insulin-dependent and insulin-independent mechanisms. As such, the modified ITPs are useful as primary agents for the treatment of type II diabetes mellitus and as adjunctive agents for the treatment of type I diabetes mellitus.

The use of an effective amount of modified ITPs as a treatment for diabetes mellitus has the advantage of being more potent than non modified ITPs. Since the modified ITPs are move stable in vivo, smaller amounts of the molecule can be administered for effective treatment. The present invention is especially suited for the treatment of patients with diabetes, both type I and type II, in that the action of the peptide is dependent on the glucose concentration of the blood, and thus the risk of hypoglycemic side effects are greatly reduced over the risks in using current methods of treatment.

The present invention also provides for a method for treating diabetes mellitus in an individual, wherein said method comprises providing an amount of modified ITP sufficient to treat diabetes; where the composition contains a modified ITP.

B. Treatment of Nervous System Disorders

The modified ITPs of the invention also find use as a sedative. In one aspect of the invention, there is provided a method of sedating a mammalian subject with an abnormality resulting in increased activation of the central or peripheral nervous system using the modified ITPs of the invention. The method comprises administering a modified ITP to the subject in an amount sufficient to produce a sedative or anxiolytic effect on the subject. The modified ITP may be administered intracerebroventriculary, orally, subcutaneously, intramuscularly, or intravenously. Such methods are useful to treat or ameliorate nervous system conditions such as anxiety, movement disorder, aggression, psychosis, seizures, panic attacks, hysteria and sleep disorders.

In a related aspect, the invention encompasses a method of increasing the activity of a mammalian subject, comprising administering a modified ITP to the subject in an amount sufficient to produce an activating effect on the subject. Preferably, the subject has a condition resulting in decreased activation of the central or peripheral nervous system. The modified ITPs find particular use in the treatment or amelioration of depression, schizoaffective disorders, sleep apnea, attention deficit syndromes with poor concentration, memory loss, forgetfulness, and narcolepsy, to name just a few conditions in which arousal of the central nervous system may be advantageous.

The modified ITPs of the invention may be used to induce arousal for the treatment or amelioration of depression, schizoaffective disorders, sleep apnea, attention deficit syndromes with poor concentration, memory loss, forgetfulness, and narcolepsy. The therapeutic efficacy of the modified ITP treatment may be monitored by patient interview to assess their condition, by psychological/neurological testing, or by amelioration of the symptoms associated with these conditions. For example, treatment of narcolepsy may be assessed by monitoring the occurrence of narcoleptic attacks. As another example, effects of modified ITPs on the ability of a subject to concentrate, or on memory capacity, may be tested using any of a number of diagnostic tests well known to those of skill in art.

C. Post Surgery Treatment

The modified ITPs of the invention may be utilized for post surgery treatments. A patient is in need of the modified ITPs of the present invention for about 1-16 hours before surgery is performed on the patient, during surgery on the patient, and after the patient's surgery for a period of not more than about 5 days.

The modified ITPs of the present invention are administered from about sixteen hours to about one hour before surgery begins. The length of time before surgery when the compounds used in the present invention should be administered in order to reduce catabolic effects and insulin resistance is dependent on a number of factors. These factors are generally known to the physician of ordinary skill, and include, most importantly, whether the patient is fasted or supplied with a glucose infusion or beverage, or some other form of sustenance during the preparatory period before surgery. Other important factors include the patient's sex, weight and age, the severity of any inability to regulate blood glucose, the underlying causes of any inability to regulate blood glucose, the expected severity of the trauma caused by the surgery, the route of administration and bioavailability, the persistence in the body, the formulation, and the potency of the compound administered. A preferred time interval within which to begin administration of the modified ITPs used in the present invention is from about one hour to about ten hours before surgery begins. The most preferred interval to begin administration is between two hours and eight hours before surgery begins.

Insulin resistance following a particular type of surgery, elective abdominal surgery, is most profound on the first post-operative day, lasts at least five days, and may take up to three weeks to normalize Thus, the post-operative patient may be in need of administration of the modified ITPs used in the present invention for a period of time following the trauma of surgery that will depend on factors that the physician of ordinary skill will comprehend and determine. Among these factors are whether the patient is fasted or supplied with a glucose infusion or beverage, or some other form of sustenance following surgery, and also, without limitation, the patient's sex, weight and age, the severity of any inability to regulate blood glucose, the underlying causes of any inability to regulate blood glucose, the actual severity of the trauma caused by the surgery, the route of administration and bioavailability, the persistence in the body, the formulation, and the potency of the compound administered. The preferred duration of administration of the compounds used in the present invention is not more than five days following surgery.

D. Insulin Resistance Treatment

The modified ITPs of the invention may be utilized to treat insulin resistance independently from their use in post surgery treatment. Insulin resistance may be due to a decrease in binding of insulin to cell-surface receptors, or to alterations in intracellular metabolism. The first type, characterized as a decrease in insulin sensitivity, can typically be overcome by increased insulin concentration. The second type, characterized as a decrease in insulin responsiveness, cannot be overcome by large quantities of insulin. Insulin resistance following trauma can be overcome by doses of insulin that are proportional to the degree of insulin resistance, and thus is apparently caused by a decrease in insulin sensitivity.

The dose of modified ITPs effective to normalize a patient's blood glucose level will depend on a number of factors, among which are included, without limitation, the patient's sex, weight and age, the severity of inability to regulate blood glucose, the underlying causes of inability to regulate blood glucose, whether glucose, or another carbohydrate source, is simultaneously administered, the route of administration and bioavailability, the persistence in the body, the formulation, and the potency.

5. Administration of the Modified ITPs

The modified ITPs will be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The modified ITPs will for the most part be administered orally, parenterally, such as intravascularly (IV), intraarterially (IA), intramuscularly (IM), subcutaneously (SC), or the like. Administration may in appropriate situations be by transfusion. In some instances, where reaction of the functional group is relatively slow, administration may be oral, nasal, rectal, transdermal or aerosol, where the nature of the conjugate allows for transfer to the vascular system. Usually a single injection will be employed although more than one injection may be used, if desired. The modified ITPs may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Other routes may find use where the administration is coupled with slow release techniques or a protective matrix. The intent is that the ITPs be effectively distributed in the blood, so as to be able to react with the blood components. The concentration of the conjugate will vary widely, generally ranging from about 1 pg/ml to 50 mg/ml. The total administered intravascularly will generally be in the range of about 0.1 mg/ml to about 10 mg/ml, more usually about 1 mg/ml to about 5 mg/ml.

By bonding to long-lived components of the blood, such as immunoglobulin, serum albumin, red blood cells and platelets, a number of advantages ensue. The activity of the modified ITPs compound is extended for days to weeks. Only one administration need be given during this period of time. Greater specificity can be achieved, since the active compound will be primarily bound to large molecules, where it is less likely to be taken up intracellularly to interfere with other physiological processes.

The formation of the covalent bond between the blood component may occur in vivo or ex vivo. For ex vivo covalent bond formation, the modified ITP is added to blood, serum or saline solution containing human serum albumin or IgG to permit covalent bond formation between the modified ITP and the blood component. In a preferred format, the ITP is modified with maleimide and it is reacted with human serum albumin in saline solution. Once the modified ITP has reacted with the blood component, to form a ITP-protein conjugate, the conjugate may be administered to the patient.

Alternatively, the modified ITP may be administered to the patient directly so that the covalent bond forms between the modified ITP and the blood component in vivo.

6. Monitoring the Presence of Modified ITPs

The blood of the mammalian host may be monitored for the activity of the ITPs and/or presence of the modified ITPs. By taking a portion or sample of the blood of the host at different times, one may determine whether the ITP has become bound to the long-lived blood components in sufficient amount to be therapeutically active and, thereafter, the level of ITP compound in the blood. If desired, one may also determine to which of the blood components the ITP molecule is bound. This is particularly important when using non-specific ITPs. For specific maleimide-ITPs, it is much simpler to calculate the half life of serum albumin and IgG.

The modified GLPs may be monitored using assays of insulinotropic activity, HPLC-MS or antibodies directed to ITPs.

A. Assays of Insulinotropic Activity

The present invention concerns modified ITPs derivatives which have an insulinotropic activity that exceeds or equals the insulinotropic activity of the non-modified ITPs. The insulinotropic property of a compound may be determined by providing that compound to animal cells, or injecting that compound into animals and monitoring the release of immunoreactive insulin (IRI) into the media or circulatory system of the animal, respectively. The presence of IRI is detected through the use of a radioimmunoassay which can specifically detect insulin.

Although any radioimmunoassay capable of detecting the presence of IRI may be employed, it is preferable to use a modification of the assay method of Albano, J. D. M., et at., (Acta Endocdnol. 70:487-509 (1972)). In this modification, a phosphate/albumin buffer with a pH of 7.4 is employed. The incubation is prepared with the consecutive condition of 500 μl of phosphate buffer, 50 μl of perfusate sample or rat insulin standard in perfusate, 100 μl of anti-insulin antiserum (Wellcome Laboratories; 1:40,000 dilution), and 100 μl of [$^{125}$I] insulin, giving a total volume of 750 μl in a 10×75-mm disposable glass tube. After incubation for 2-3 days at 4° C., free insulin is separated from antibody-bound insulin by charcoal separation. The assay sensitivity is generally 1-2 μU/ml. In order to measure the release of IRI into the cell culture medium of cells grown in tissue culture, one preferably incorporates radioactive label into proinsulin. Although any radioactive label capable of labeling a polypeptide can be used, it is preferable to use $^3$H leucine in order to obtain labeling of proinsulin. Labeling can be done for any period of time sufficient to permit the formation of a detectably labeled pool of proinsulin molecules; however, it is preferable to incubate cells in the presence of radioactive label for a 60-minute time period. Although any cell line capable of expressing insulin can be used for determining whether a compound has an insulinotropic effect, it is preferable to use rat insulinoma cells, and especially RIN-38 rat insulinoma cells. Such cells can be grown in any suitable medium; however, it is preferable to use DME medium containing 0.1% BSA and 25 mM glucose.

The insulinotropic property of a modified ITP may also be determined by pancreatic infusion. The in situ isolated perfused rat pancreas preparation is a modification of the method of Penhos, J. C., et al. (Diabetes 18:733-738 (1969)). In accordance with such a method, fasted rats (preferably male Charles River strain albino rats), weighing 350-600 g, are anesthetized with an intraperitoneal injection of Amytal Sodium (Eli Lilly and Co., 160 ng/kg). Renal, adrenal, gastric, and lower colonic blood vessels are ligated. The entire intestine is resected except for about four cm of duodenum and the descending colon and rectum. Therefore, only a small part of the intestine is perfused, thus minimizing possible interference by enteric substances with insulinotropic immunoreactivity. The perfusate is preferably a modified Krebs-Ringer bicarbonate buffer with 4% dextran T70 and 0.2% bovine serum albumin (fraction V), and is preferably bubbled with 95% $O_2$ and 5% $CO_2$. A nonpulsatile flow, four-channel roller-bearing pump (Buchler polystatic, Buchler Instruments Division, Nuclear-Chicago Corp.) is preferably used, and a switch from one perfusate source to another is preferably accomplished by switching a three-way stopcock. The manner in which perfusion is performed, modified, and analyzed preferably follows the methods of Weir, G. C., et al., (J. Clin. Investigat. 54:1403-1412 (1974)), which is hereby incorporated by reference.

B. HPLC-MS

HPLC coupled with mass spectrometry (MS) with can be utilized to assay for the presence of peptides and modified peptides as is well known to the skilled artisan. Typically two mobile phases are utilized: 0.1% TFA/water and 0.1% TFA/acetonitrile. Column temperatures can be varied as well as gradient conditions. Particular details are outlined in the Example section below.

C. Antibodies

Another aspect of this invention relates to methods for determining the concentration of the ITPs or their conjugates in biological samples (such as blood) using antibodies specific to the ITPs and to the use of such antibodies as a treatment for toxicity potentially associated with such ITPs or conjugates. This is advantageous because the increased stability and life of the ITPs in vivo in the patient might lead to novel problems during treatment, including increased possibility for toxicity. The use of anti-ITP antibodies, either monoclonal or polyclonal, having specificity for particular ITPs, can assist in mediating any such problem. The antibody may be generated or derived from a host immunized with the particular modified ITP, or with an immunogenic fragment of the agent, or a synthesized immunogen corresponding to an antigenic determinant of the agent. Preferred antibodies will have high specificity and affinity for native, derivatized and conjugated forms of the modified ITP. Such antibodies can also be labeled with enzymes, fluorochromes, or radiolables.

Antibodies specific for modified ITPs may be produced by using purified ITPs for the induction of derivatized ITP-specific antibodies. By induction of antibodies, it is intended not only the stimulation of an immune response by injection into animals, but analogous steps in the production of synthetic antibodies or other specific binding molecules such as screening of recombinant immunoglobulin libraries. Both monoclonal and polydonal antibodies can be produced by procedures well known in the art.

The antibodies may be used to monitor the presence of ITP peptides in the blood stream. Blood and/or serum samples may be analyzed by SDS-PAGE and western blotting. Such techniques permit the analysis of the blood or serum to determine the bonding of the modified ITPs to blood components.

The anti-therapeutic agent antibodies may also be used to treat toxicity induced by administration of the modified ITP, and may be used ex vivo or in vivo. Ex vivo methods would include immuno-dialysis treatment for toxicity employing anti-therapeutic agent antibodies fixed to solid supports. In vivo methods include administration of anti-therapeutic agent antibodies in amounts effective to induce clearance of antibody-agent complexes.

The antibodies may be used to remove the modified ITPs and conjugates thereof, from a patients blood ex vivo by contacting the blood with the antibodies under sterile conditions. For example, the antibodies can be fixed or otherwise immobilized on a column matrix and the patient's blood can be removed from the patient and passed over the matrix. The modified ITPs will bind to the antibodies and the blood containing a low concentration of the ITP, then may be returned to the patient's circulatory system. The amount of modified ITP removed can be controlled by adjusting the pressure and flow rate. Preferential removal of the modified ITPs from the plasma component of a patient's blood can be effected, for example, by the use of a semipermeable membrane, or by otherwise first separating the plasma component from the cellular component by ways known in the art prior to passing the plasma component over a matrix containing the anti-therapeutic antibodies. Alternatively the preferential removal of ITP-conjugated blood cells, including red blood cells, can be effected by collecting and concentrating the blood cells in the patient's blood and contacting those cells with fixed anti-ITP antibodies to the exclusion of the serum component of the patient's blood.

The anti-ITP antibodies can be administered in vivo, parenterally, to a patient that has received the modified ITP or conjugates for treatment. The antibodies will bind the ITP compounds and conjugates. Once bound, the ITP activity will be hindered if not completely blocked thereby reducing the biologically effective concentration of ITP compound in the patient's bloodstream and minimizing harmful side effects. In addition, the bound antibody-ITP complex will facilitate clearance of the ITP compounds and conjugates from the patient's blood stream.

The invention having been fully described is now exemplified by the following non-limiting examples.

EXAMPLES

General

Solid phase peptide syntheses of the insulinotropic peptides on a 100 μmole scale was performed using manual solid-phase synthesis and a Symphony Peptide Synthesizer using Fmoc protected Rink Amide MBHA resin, Fmoc protected amino acids, O-benzotriazol-1-yl-N,N,N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). When required, the selective deprotection of the Lys(Aloc) group was performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin was then washed with $CHCl_3$ (6×5 mL), 20% HOAc in DCM (6×5 mL), DCM (6×5 mL), and DMF (6×5 mL). In some instances, the synthesis was then re-automated for the addition of one AEEA (aminoethoxyethoxyacetic acid) group, the addition of acetic acid or the addition of a 3-maleimidopropionic acid (MPA) (Step 3). Resin cleavage and product isolation was performed using 85% TFA/5% TIS/5% thioanisole and 5% phenol, followed by precipitation by dry-ice cold $Et_2O$ (Step 4). The products were purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at 214 and 254 nm. Purity was determined 95% by RP-HPLC mass spectrometry using a Hewlett Packard LCMS-1100 series spectrometer equipped with a diode array detector and using electro-spray ionization.

Example 1

Preparation of $Tyr^{32}$-Exendin 4(1-32)-$NH_2$

```
His-Gly-Glu-Gly-Thr-Phe-Thr-Ser-         (SEQ ID NO: 35)
Asp-Leu-Ser-Lys-Gln-Met-Glu-Glu-Glu-
Ala-Val-Arg-Leu-Phe-Ile-Glu-Trp-Leu-
Lys-Asn-Gly-Gly-Pro-Tyr-amide
```

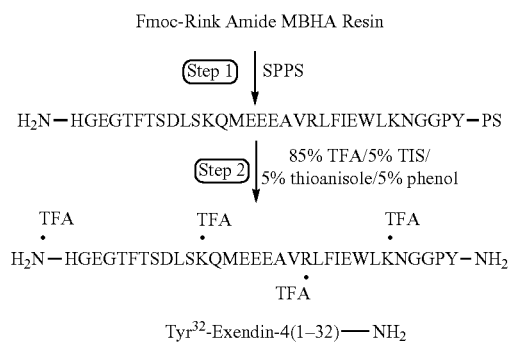

Solid phase peptide synthesis of the analog on a 100 pmole scale is performed using manual solid-phase synthesis and a Symphony Peptide Synthesizer using Fmoc protected Rink Amide MBHA resin, Fmoc protected amino acids, O-benzotriazol-1-yl-N,N,N',N'-tetramethyl-uronium hexafluorophosphate (HBTU) in N,N-dimethylformamide (DMF) solution and activation with N-methyl morpholine (NMM), and piperidine deprotection of Fmoc groups (Step 1). Resin cleavage and product isolation is performed using 85% TFA/5% TIS/5% thioanisole and 5% phenol, followed by precipitation by dry-ice cold $Et_2O$ (Step 2). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired peptide in >95% purity, as determined by RP-HPLC.

Example 2

Preparation of Tyr³¹-Exendin-4(1-31)

```
His-Gly-Glu-Gly-Thr-Phe-Thr-Ser-        (SEQ ID NO: 23)
Asp-Leu-Ser-Lys-Gln-Met-Glu-Glu-Glu-
Ala-Val-Arg-Leu-Phe-Ile-Glu-Trp-Leu-
Lys-Asn-Gly-Gly-Tyr-amide
```

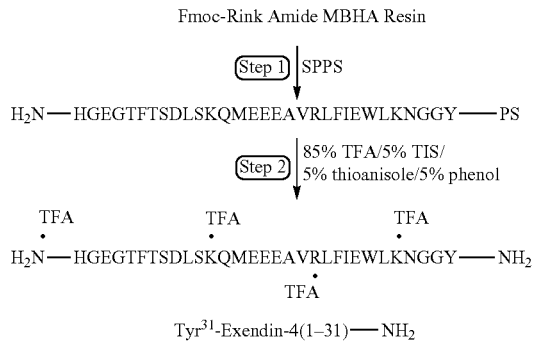

Solid phase peptide synthesis of the analog on a 100 μmole scale is performed using manual solid-phase synthesis and a Symphony Peptide Synthesizer using Fmoc protected Rink Amide MBHA resin, Fmoc protected amino acids, O-benzotriazol-1-yl-N,N,N',N'-tetramethyl-uronium hexafluorophosphate (HBTU) in N,N-dimethylformamide (DMF) solution and activation with N-methyl morpholine (NMM), and piperidine deprotection of Fmoc groups (Step 1). Resin cleavage and product isolation is performed using 85% TFA/5% TIS/5% thioanisole and 5% phenol, followed by precipitation by dry-ice cold Et₂O (Step 2). The product is purified by preparative reversed phased HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired peptide in >95% purity, as determined by RP-HPLC.

Example 3

Preparation of Exendin-4(9-39)-NH₂

```
Asp-Leu-Ser-Lys-Gln-Met-Glu-Glu-        (SEQ ID NO: 24)
Glu-Ala-Val-Arg-Leu-Phe-Ile-Glu-Trp-
Leu-Lys-Asn-Gly-Gly-Pro-Ser-Ser-Gly-
Ala-Pro-Pro-Pro-Ser-amide
```

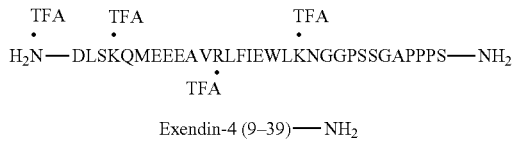

Solid phase peptide synthesis of the analog on a 100 μmole scale is performed using manual solid-phase synthesis and a Symphony Peptide Synthesizer using Fmoc protected Rink Amide MBHA resin, Fmoc protected amino acids, O-benzotriazol-1-yl-N,N,N',N'-tetramethyl-uronium hexafluorophosphate (HBTU) in N,N-dimethylformamide (DMF) solution and activation with N-methyl morpholine (NMM), and piperidine deprotection of Fmoc groups (Step 1). Resin cleavage and product isolation is performed using 85% TFA/5% TIS/5% thioanisole and 5% phenol, followed by precipitation by dry-ice cold Et₂O (Step 2). The product is purified by preparative reversed phased HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired peptide in >95% purity, as determined by RP-HPLC.

Example 4

Preparation of GLP-1 (1-36)-Lys³⁷(ε-MPA)-NH₂.5TFA

```
His-Asp-Glu-Phe-Glu-Arg-His-Ala-        (SEQ ID NO: 25)
Glu-Gly-Thr-Phe-Thr-Ser-Asp-Val-Ser-
Ser-Tyr-Leu-Glu-Gly-Gln-Ala-Ala-Lys-
Glu-Phe-Ile-Ala-Trp-Leu-Val-Lys-Gly-
Arg-Lys(ε-MPA)-NH₂.5TFA
```

The modified GLP-1 peptide is synthesized by linking off the amino group of the added Lysine residue as shown in the schematic diagram below.

Fmoc-Rink Amide MBHA Resin

[Step 1] SPPS

Boc—HDEFERHAEGTFTSDVSSYLEGQAAKEFIAWLVKGR-Lys(Aloc)—PS

[Step 2] Pd(PPh₃)₄/NMM/HOAc/CHCl₃

-continued

Boc—HDEFERHAEGTFTSDVSSYLEGQAAKEFIAWLVKGR-Lys—PS

Step 3 | 3-maleimidopropionic acid

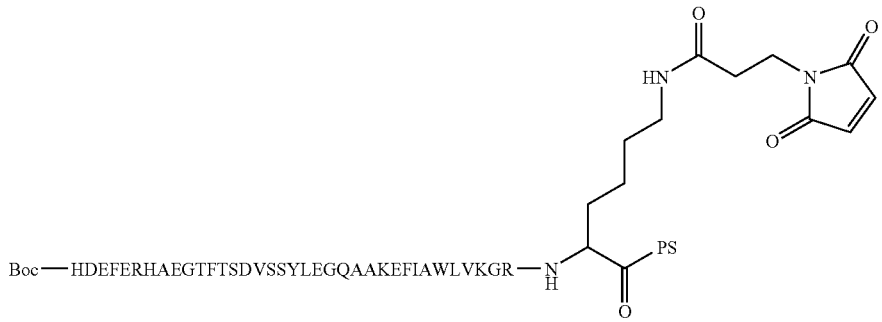

Boc—HDEFERHAEGTFTSDVSSYLEGQAAKEFIAWLVKGR—NH

Step 4 | 85% TFA/5% TIS/5% thioanisole/5% phenol

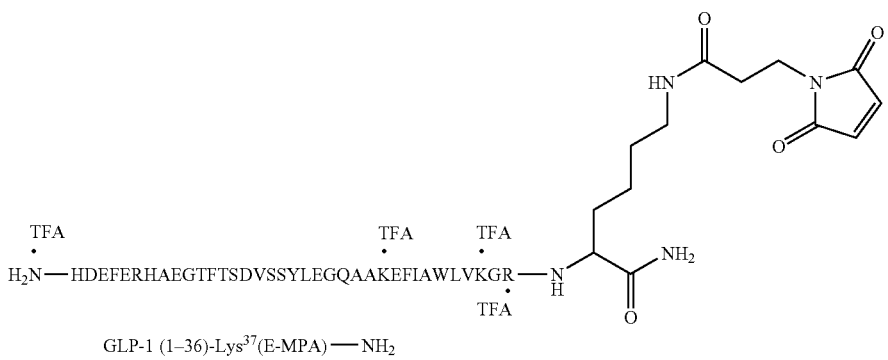

TFA • TFA • TFA
H₂N—HDEFERHAEGTFTSDVSSYLEGQAAKEFIAWLVKGR—NH
• TFA

GLP-1 (1–36)-Lys³⁷(E-MPA)—NH₂

Using automated peptide synthesis, the following protected amino acids were sequentially added to Rink Amide MBHA resin: Fmoc-Lys(Aloc)-OH, Fmoc-Arg(Pbf)-OH, Fmoc-Gly-OH, Fmoc-Lys(tBoc)-OH, Fmoc-Val-OH, Fmoc-Leu-OH, Fmoc-Trp-OH, Fmoc-Ala-OH, Fmoc-Ile-OH, Fmoc-Phe-OH, Fmoc-Glu(OtBu)-OH, Fmoc-Lys(tBoc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(Pbf)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(N-Trt)-OH, Fmoc-Arg(Pbf)-OH, Fmoc-Glu(OtBu)-OH, Fmoc-Phe-OH, Fmoc-Glu(OtBu)-OH, Fmoc-Asp(OtBu)-OH, Boc-His(N-Trt)-OH (step 1)

The selective deprotection of the Lys(Aloc) group was performed manually and accomplished by treating the resin with a solution of 3 eq of Pd(PPh₃)₄ dissolved in 5 mL of CHCl₃:NMM:HOAc (18:1:0.5) for 2 h (Step 2). The resin was then washed with CHCl₃ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et₂O (Step 4). The product was purified by preparative reverse phase HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10µ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 5

Preparation of GLP-1 (1-36)-Lys³⁷(ε-AEEA-AEEA-MPA)-NH₂.5TFA

```
His-Asp-Glu-Phe-Glu-Arg-His-Ala-         (SEQ ID NO: 26)
Glu-Gly-Thr-Phe-Thr-Ser-Asp-Val-Ser-
Ser-Tyr-Leu-Glu-Gly-Gln-Ala-Ala-Lys-
Glu-Phe-Ile-Ala-Trp-Leu-Val-Lys-Gly-
Arg-Lys(ε-AEEA-AEEA-MPA)-NH₂.5TFA
```

The modified GLP-1 peptide is synthesized by linking off the amino group of the added Lysine residue as shown in the schematic diagram below.

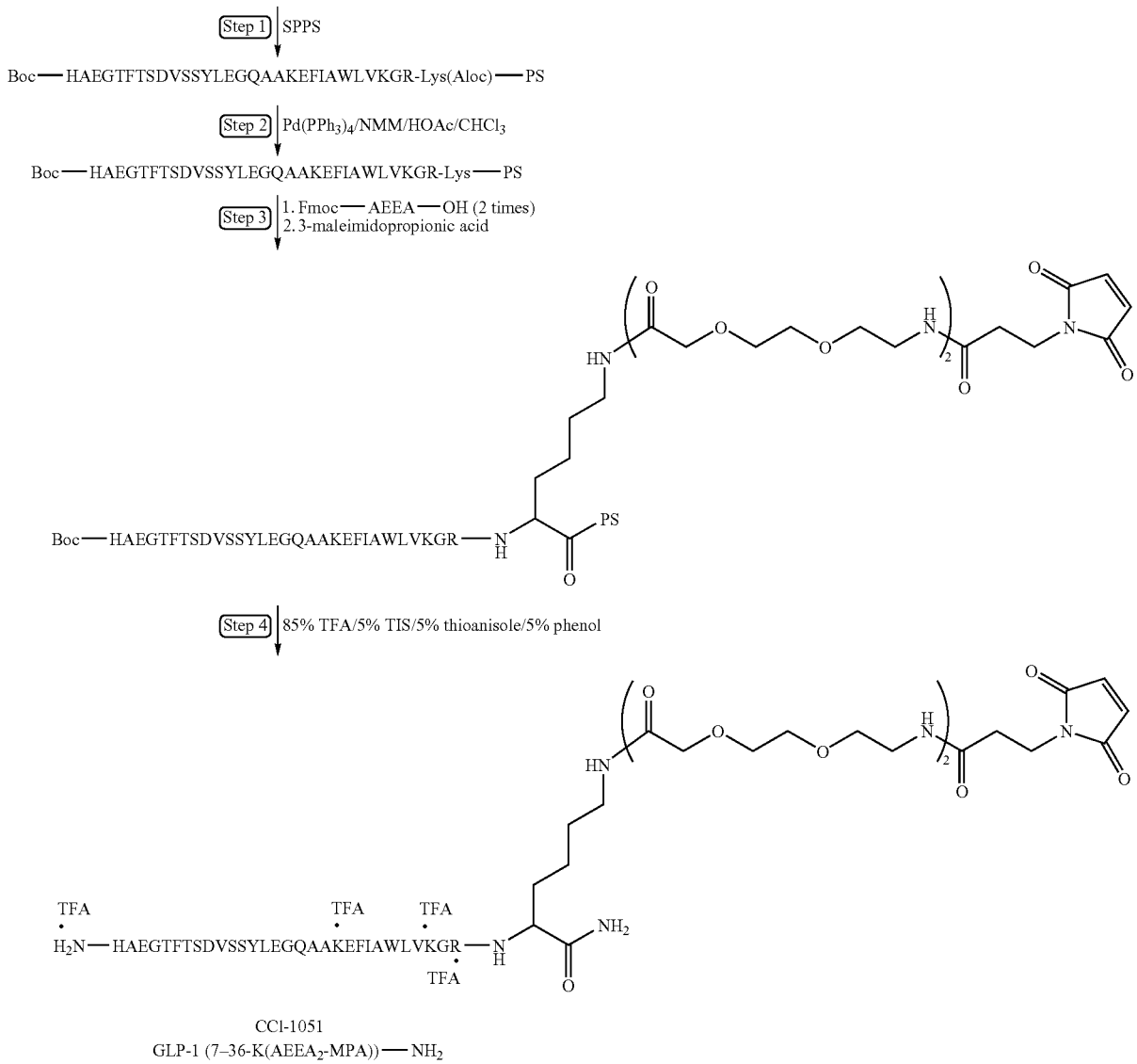

CCl-1051
GLP-1 (7–36-K(AEEA$_2$-MPA))—NH$_2$

Using automated peptide synthesis, the following protected amino acids were sequentially added to Rink Amide MBHA resin: Fmoc-Lys(Aloc)-OH, Fmoc-Arg(Pbf)-OH, Fmoc-Gly-OH, Fmoc-Lys(tBoc)-OH Fmoc-Val-OH, Fmoc-Leu-OH, Fmoc-Trp-OH, Fmoc-Ala-OH, Fmoc-Ile-OH, Fmoc-Phe-OH, Fmoc-Glu(OtBu)-OH, Fmoc-Lys(tBoc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(Pbf)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(N-Trt)-OH, Fmoc-Arg(Pbf)-OH, Fmoc-Glu(OtBu)-OH, Fmoc-Phe-OH, Fmoc-Glu(OtBu)-OH, Fmoc-Asp(OtBu)OH, Boc-His(N-Trt)-OH (step 1).

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the two AEEA (aminoethoxyethoxyacetic acid) groups and the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization, ESI-MS m/z for C$_{174}$H$_{265}$N$_{44}$O$_{56}$ (MH$^+$), calcd 3868. Found [M+H$_2$]$^{2+}$1934, [M+H$_3$]$^{3+}$1290, [M+H$_4$]$^{4+}$967.

Example 6

Preparation of GLP-1 (7-36)-Lys$^{37}$(ε-MPA)-NH$_2$.4TFA

```
His-Ala-Glu-Gly-Thr-Phe-Thr-Ser-        (SEQ ID NO: 27)
Asp-Val-Ser-Ser-Tyr-Leu-Glu-Gly-Gln-
Ala-Ala-Lys-Glu-Phe-Ile-Ala-Trp-Leu-
Val-Lys-Gly-Arg-Lys(ε-MPA)-NH2.4TFA
```

The modified GLP-1 peptide is synthesized by linking off the ε-N terminus of the added Lysine residue as described below.

Using automated peptide synthesis, the following protected amino acids were sequentially added to Rink Amide MBHA resin: Fmoc-Lys(Aloc)-OH, Fmoc-Arg(Pbf)-OH, Fmoc-Gly-OH, Fmoc-Lys(tBoc)-OH, Fmoc-Val-OH, Fmoc-Leu-OH, Fmoc-Trp-OH, Fmoc-Ala-OH, Fmoc-Ile-OH, Fmoc-Phe-OH, Fmoc-Glu(OtBu)-OH, Fmoc-Lys(tBoc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(Pbf)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(N-Trt)-OH (Step 1).

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFP/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 7

Preparation of GLP-1 (7-36)-Lys$^{37}$(ε-AEEA-AEEA-MPA)-NH$_2$.4TFA

```
His-Ala-Glu-Gly-Thr-Phe-Thr-Ser-        (SEQ ID NO: 28)
Asp-Val-Ser-Ser-Tyr-Leu-Glu-Gly-Gln-
Ala-Ala-Lys-Glu-Phe-Ile-Ala-Trp-Leu-
Val-Lys-Gly-Arg-Lys(ε-AEEA-AEEA-
MPA)-
NH2.4TFA
```

The modified GLP-1 peptide is synthesized by linking off the ε-N terminus of the added Lysine residue as described below.

Using automated peptide synthesis, the following protected amino acids were sequentially added to Rink Amide MBHA resin: Fmoc-Lys(Aloc)-OH, Fmoc-Arg(Pbf)-OH, Fmoc-Gly-OH, Fmoc-Lys(tBoc)-OH, Fmoc-Val-OH, Fmoc-Leu-OH, Fmoc-Trp-OH, Fmoc-Ala-OH, Fmoc-Ile-OH, Fmoc-Phe-OH, Fmoc-Glu(OtBu)-OH, Fmoc-Lys(tBoc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(Pbf)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(N-Trt)-OH (Step 1).

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the two AEEA (aminoethoxyethoxyacetic acid) groups and the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 8

Preparation of D-Ala$^8$ GLP-1 (7-36)-Lys$^{37}$(ε-MPA)-NH$_2$.4TFA

```
His-D-Ala-Glu-Gly-Thr-Phe-Thr-          (SEQ ID NO: 29)
Ser-Asp-Val-Ser-Ser-Tyr-Leu-Glu-Gly-
Gln-Ala-Ala-Lys-Glu-Phe-Ile-Ala-Trp-
Leu-Val-Lys-Gly-Arg-Lys(ε-MPA)-
NHH2.4TFA
```

D-Ala$^8$ GLP-1 (7-36) amide was synthesized as shown in the schematic diagram below.

A. Preparation of D-Ala$^8$-GLP-1 (7-36) amide

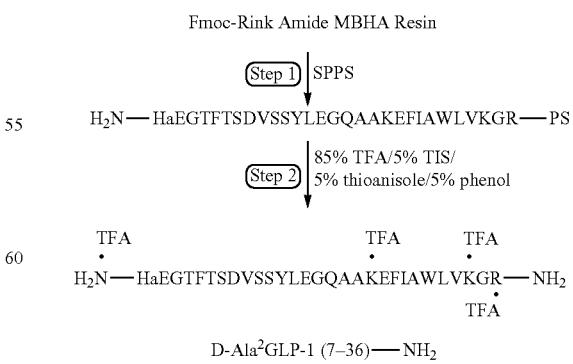

Solid phase peptide synthesis of the GLP-1 analog on a 100 µmole scale is performed using manual solid-phase synthesis and a Symphony Peptide Synthesizer using Fmoc protected Rink Amide MBHA resin, Fmoc protected amino acids, O-benzotriazol-1-yl-N,N,N',N'-tetramethyl-uronium hexafluorophosphate (HBTU) in N,N-dimethylformamide (DMF) solution and activation with N-methyl morpholine (NMM), and piperidine deprotection of Fmoc groups (Step 1). Resin cleavage and product isolation is performed using 85% TFA/5% TIS/5% thioanisole and 5% phenol, followed by precipitation by dry-ice cold $Et_2O$ (Step 2). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired peptide in >95% purity, as determined by RP-HPLC.

The modified GLP-1 peptide is synthesized by linking off the ε-N terminus of the added Lysine residue as shown in the schematic diagram below.

Using automated peptide synthesis, the following protected amino acids were sequentially added to Ring Amide MBHA resin: Fmoc-Lys(Aloc)-OH, Fmoc-Arg(Pbf)-OH, Fmoc-Gly-OH, Fmoc-Lys(tBoc)-OH, Fmoc-Val-OH, Fmoc-Leu-OH, Fmoc-Trp-OH, Fmoc-Ala-OH, Fmoc-ile-OH, Fmoc-Phe-OH, Fmoc-Glu(OtBu)-OH, Fmoc-Lys(tBoc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(Pbf)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(N-Trt)-OH (Step 1).

The selective deprotection of the Lys(Aloc) group was performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin was then washed with $CHCl_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold $Et_2O$ (Step 4). The product was purified by preparative reverse phase HPLC using a Varian (Rainin) preparative binary HPLC system: gradient elution of 30-55% B (0.045%

B. Preparation of D-Ala²-GLP-1 (7-36)-Lys³⁷ (E-MPA) amide

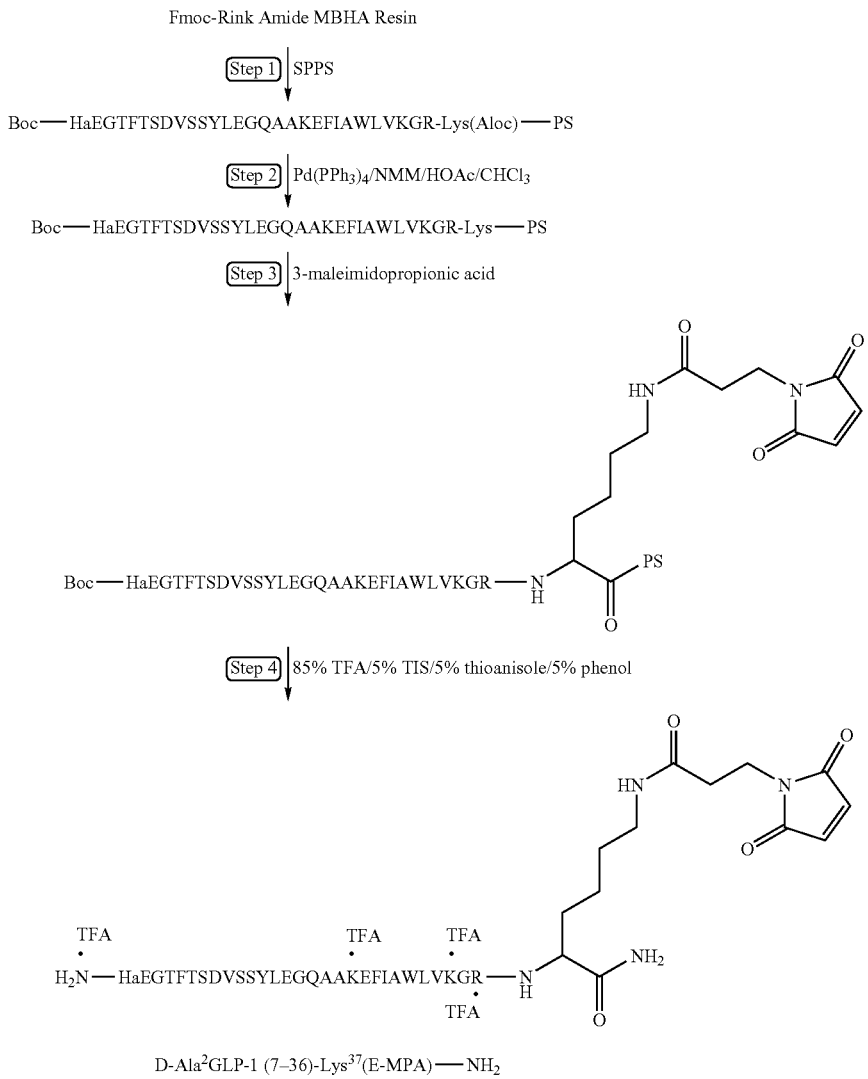

D-Ala²GLP-1 (7–36)-Lys³⁷(E-MPA)—NH₂

TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ214 and 254 nm. The product had >95% purity at determined by RP-HPLC mass spectrometry using a Hewlett Packard LCMS-1100 series spectrometer equipped with a diode array detector and using electro-spray ionization.

Example 9

Preparation of D-Ala⁸ GLP-1 (7-36)-Lys³⁷(ε-AEEA-AEEA-MPA)-NH₂.4TFA

```
His-D-Ala-Glu-Gly-Thr-Phe-Thr-          (SEQ ID NO: 30)
Ser-Asp-Val-Ser-Ser-Tyr-Leu-Glu-Gly-
Gln-Ala-Ala-Lys-Glu-Phe-Ile-Ala-Trp-
Leu-Val-Lys-Gly-Arg-Lys (ε-AEEA-
AEEA-
MPA)-NH₂.4TFA
```

The modified GLP-1 peptide is synthesized by linking off the □-N terminus of the added Lysine residue as shown in the schematic diagram below.

Using automated peptide synthesis, the following protected amino acids were sequentially added to Rink Amide MBHA resin: Fmoc-Lys(Aloc)-OH, Fmoc-Arg(Pbf)-OH, Fmoc-Gly-OH, Fmoc-Lys(tBoc)-OH, Fmoc-Val-OH, Fmoc-Leu-OH, Fmoc-Trp-OH, Fmoc-Ala-OH, Fmoc-Ile-OH, Fmoc-Phe-OH, Fmoc-Glu(OtBu)-OH, Fmoc-Lys(tBoc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(Pbf)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(N-Trt)-OH (Step 1).

The selective deprotection of the Lys(Aloc) group was performed manually and accomplished by treating the resin with a solution of 3 eq of Pd(PPh₃)₄ dissolved in 5 mL of CHCl₃:NMM:HOAc (18:1:0.5) for 2 h (Step 2). The resin was then washed with CHCl₃ (6×5 mL), 20% HOAc in DCM (6×5 mL), DCM (6×5 mL), and DMF (6×5 mL). The synthesis was then re-automated for the addition of the two AEEA (aminoethoxyethoxyacetic acid) groups and the 3-maleimi-

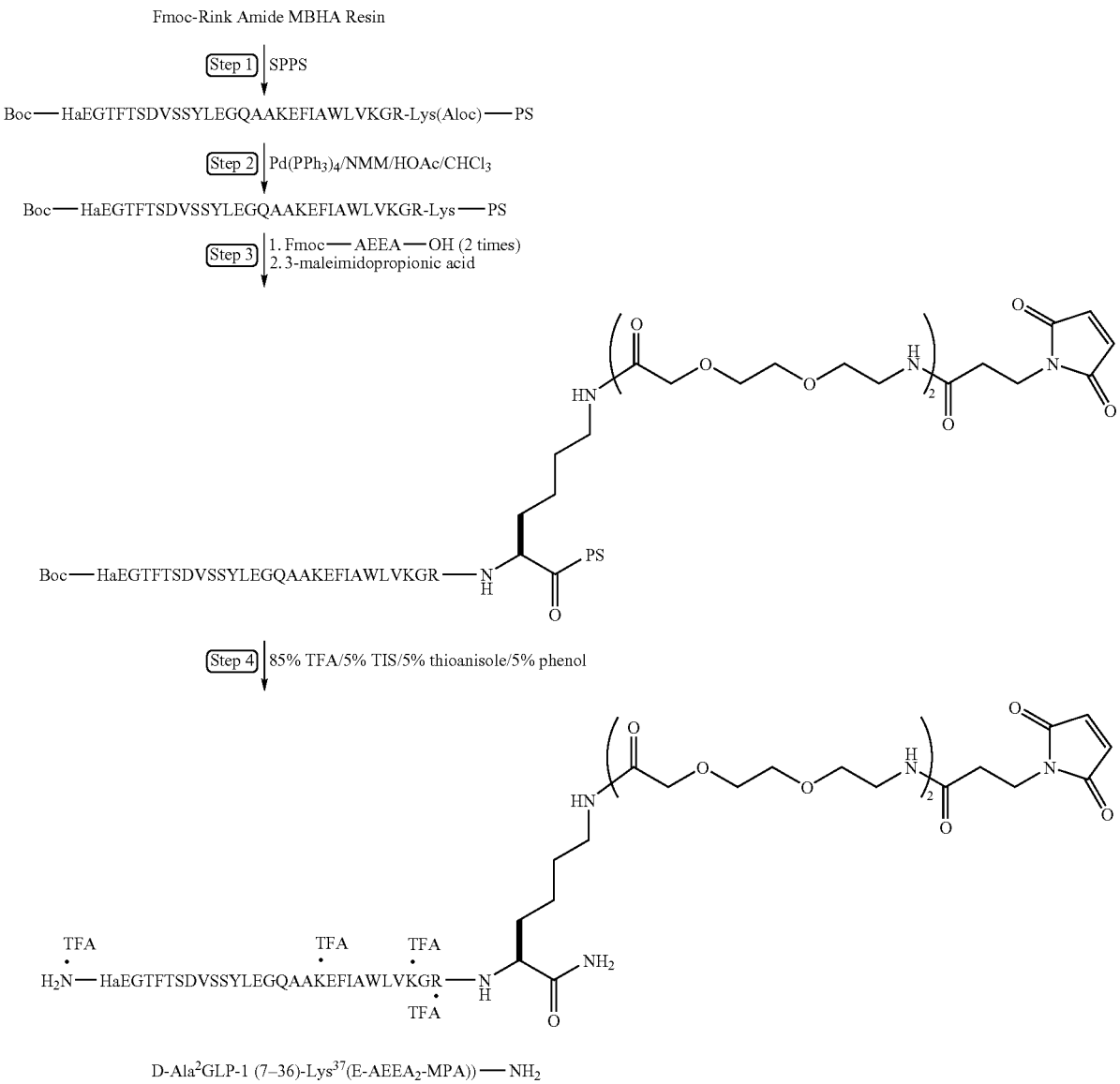

D-Ala²GLP-1 (7–36)-Lys³⁷(E-AEEA₂-MPA))—NH₂ dopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 10

Preparation of Exendin-4 (1-39)-Lys$^{40}$(ϵ-MPA)-NH$_2$

```
His-Gly-Glu-Gly-Thr-Phe-Thr-Ser-        (SEQ ID NO: 31)
Asp-Leu-Ser-Lys-Gln-Met-Glu-Glu-Glu-
Ala-Val-Arg-Leu-Phe-Ile-Glu-Trp-Leu-
Lys-Asn-Gly-Gly-Pro-Ser-Ser-Gly-Ala-
Pro-Pro-Pro-Ser-Lys (ϵ-MPA)-NH$_2$.5TFA
```

Exendin-4 is synthesized as shown in the schematic below.

A. Preparation of Exendin 4

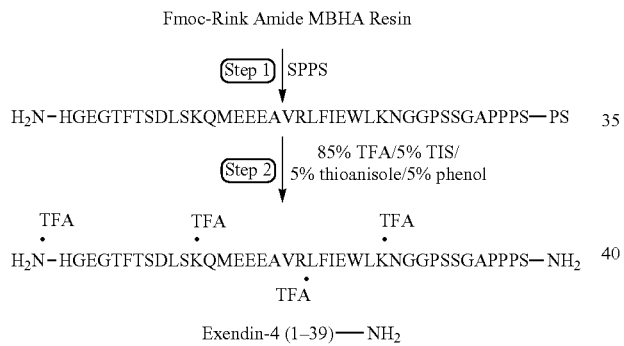

Solid phase peptide synthesis of Exendin-4 on a 100 µmole scale is performed using manual solid-phase synthesis and a Symphony Peptide Synthesizer using Fmoc protected Rink Amide MBHA resin The following protected amino acids are sequentially added to the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg(Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Boc-His(Trt)-OH. They are dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group is achieved using a solution of 20% (V/N) piperidine in N,N-dimethylformamide (DMF) for 20 minutes (Step 1). Resin cleavage and product isolation is performed using 85% TFA/5% TIS/5% thioanisole and 5% phenol, followed by precipitation by dry-ice cold Et$_2$O (Step 2). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at □214 and 254 nm to afford the desired peptide in >95% purity, as determined by RP-HPLC.

B. Preparation of Modified Exendin 4 (SEQ ID NO:31)

The modified exendin-4 peptide is synthesized by linking off the ϵ-N terminus of the added Lysine residue as shown in the schematic diagram below.

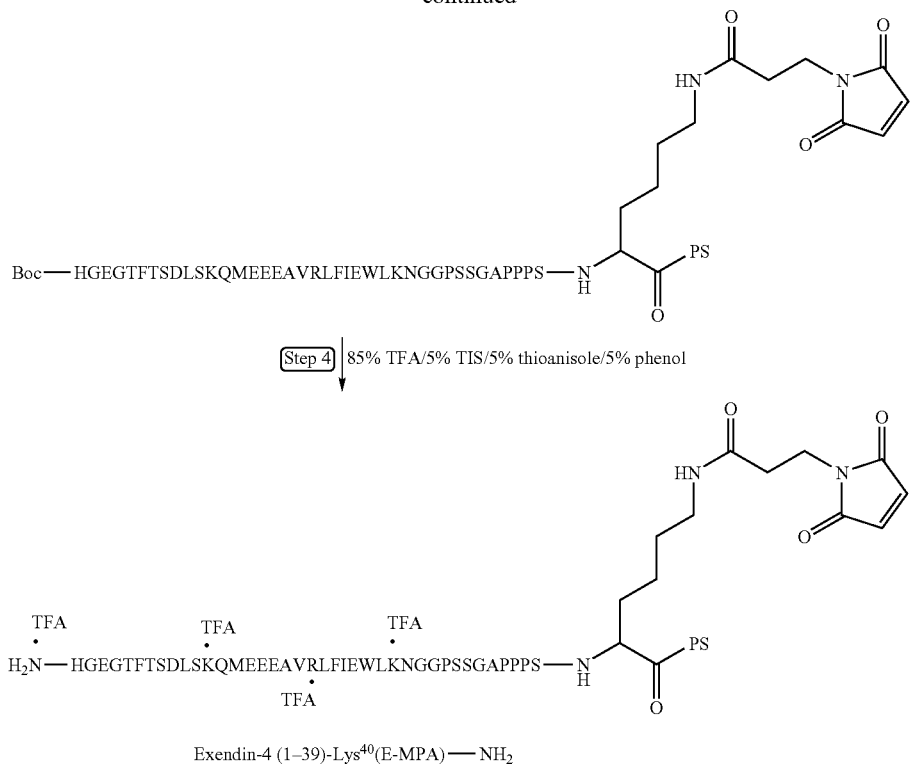

Using automated peptide synthesis, the following protected amino acids were sequentially added to Rink Amide MBHA resin: Fmoc-Lys(Aloc)-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser-OH, Fmoc-Ser(tBu)-OH, Fmoc-Pro-OH, Fmoc-Gly-OH, Fmoc-Gly-OH, Fmoc-Asn(Trt)OH, Fmoc-Lys(Boc)-OH, Fmoc-Leu-OH, Fmoc-Trp-OH, Fmoc-Glu(OtBu)-OH, Fmoc-Ile-OH, Fmoc-Phe-OH, Fmoc-Leu-OH, Fmoc-Arg(Bpf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Boc-His(Trt)-OH (Step 1).

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL). 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 11

Preparation of Modified Exendin-4 (1-39)-Lys$^{40}$(ε-AEEA-AEEA-MPA)-NH$_2$.5TFA

```
His-Gly-Glu-Gly-Thr-Phe-Thr-Ser-Asp-    (SEQ ID NO: 32)
Leu-Ser-Lys-Gln-Met-Glu-Glu-Glu-Ala-
Val-Arg-Leu-Phe-Ile-Glu-Trp-Leu-Lys-
Asn-Gly-Gly-Pro-Ser-Ser-Gly-Ala-Pro-
Pro-Pro-Ser-Lys(ε-AEEA-AEEA-MPA)-
NH₂.5TFA
```

The modified exendin-4 peptide is synthesized by linking off the ε-N terminus of the added Lysine residue as shown in the schematic diagram below.

Fmoc-Rink Amide MBHA Resin

Step 1 | SPPS

Boc—HGEGTFTSDLSKQMEEEAVRLFIEWLKNGGPSSGAPPPS-Lys(Aloc)—PS

Step 2 | Pd(PPh₃)₄/NMM/HOAc/CHCl₃

Boc—HGEGTFTSDLSKQMEEEAVRLFIEWLKNGGPSSGAPPPS-Lys—PS

Step 3 | 1. Fmoc—AEEA—OH (2 times)
2. 3-maleimidopropionic acid

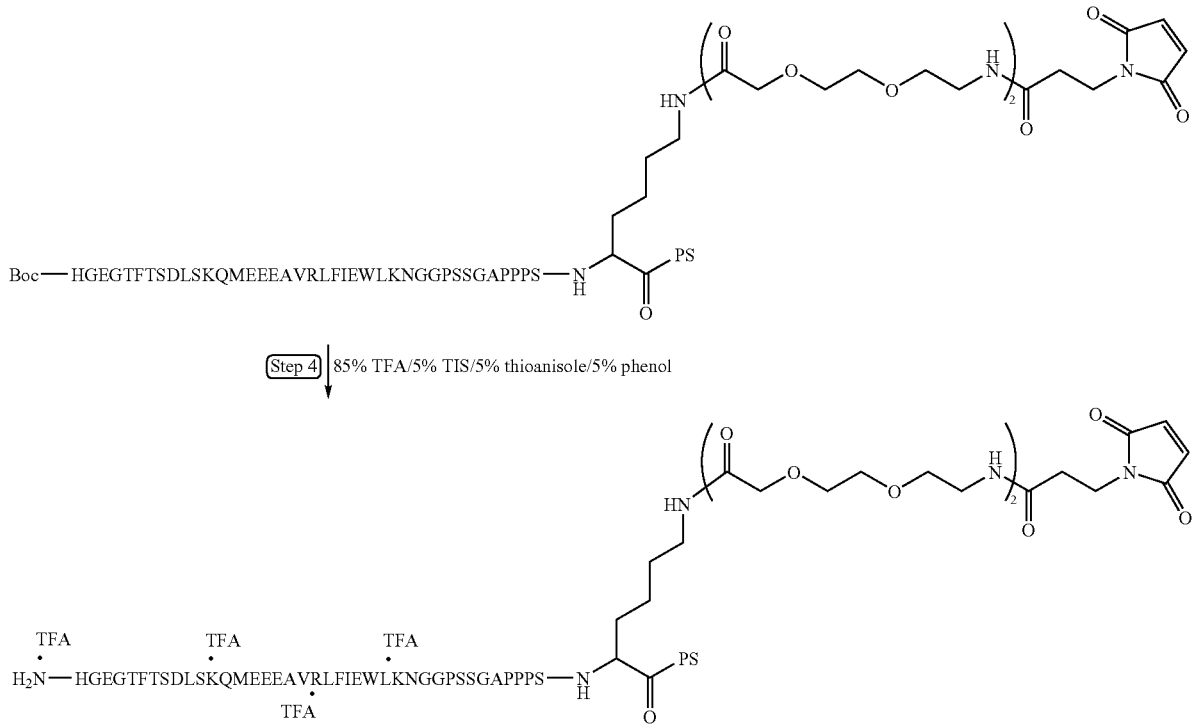

Boc—HGEGTFTSDLSKQMEEEAVRLFIEWLKNGGPSSGAPPPS—N

Step 4 | 85% TFA/5% TIS/5% thioanisole/5% phenol

TFA · TFA · TFA
H₂N—HGEGTFTSDLSKQMEEEAVRLFIEWLKNGGPSSGAPPPS—N
TFA

Exendin-4 (1–39)-Lys⁴⁰(ε-AEEA₂-MPA)—NH₂
40

Using automated peptide synthesis, the following protected amino acids were sequentially added to Rink Amide MBHA resin: Fmoc-Lys(Aloc)-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp-OH, Fmoc-Glu(OtBu)-OH, Fmoc-Ile-OH, Fmoc-Phe-OH, Fmoc-Leu-OH, Fmoc-Arg(Bpf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(OtBu)-OH, Fmoc-Leu-OH, Fmoc-Asp(OtBu)-OH, Fmoc-Ser(OtBu)-OH, Fmoc-Thr(tBu)-OH, Fmoc-Phe-OH, Fmoc-Thr(tBu)-OH, Fmoc-Gly-OH, Fmoc-Glu(OtBu)OH, Fmoc-Gly-OH, Boc-His(Trt)-OH (Step 1).

The selective deprotection of the Lys(Aloc) group was performed manually and accomplished by treating the resin with a solution of 3 eq of Pd(PPh₃)₄ dissolved in 5 mL of CHCl₃:NMM:HOAc (18:1:0.5) for 2 h (Step 2). The resin was then washed with CHCl₃ (6×5 mL), 20% HOAc in DCM (6×5 mL), DCM (6×5 mL), and DMF (6×5 mL). The synthesis was then re-automated for the addition of the two AEEA (aminoethoxyethoxyacetic acid) groups and the 3-maleimidopropionic acid (Step 3). Resin cleavage and product isolation was performed using 85% TFA/5% TIS/5% thioanisole and 5% phenol, followed by precipitation by dry-ice cold Et₂O (Step 4). The product was purified by preparative reverse phase HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10µ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 12

Preparation of Exendin-3 (1-39)-Lys⁴⁰(ε-MPA)-NH₂.5TFA

His-Ser-Asp-Gly-Thr-Phe-Thr-Ser-Asp- (SEQ ID NO: 33)
Leu-Ser-Lys-Gln-Met-Glu-Glu-Glu-Ala-
Val-Arg-Leu-Phe-Ile-Glu-Trp-Leu-Lys-
Asn-Gly-Gly-Pro-Ser-Ser-Gly-Ala-Pro-
Pro-Pro-Ser-Lys(ε-MPA)-NH₂.5TFA

43
A Preparation of Exendin 3

The exendin-3 peptide first is synthesized as described in the schematic below.

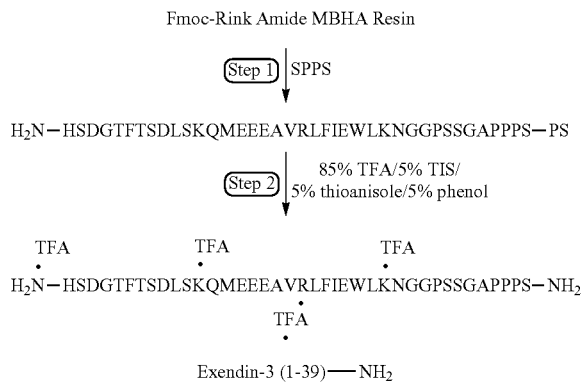

Solid phase peptide synthesis of Exendin 3 on a 100 μmole scale is performed using manual solid-phase synthesis and a Symphony Peptide Synthesizer using Fmoc protected Rink Amide MBHA resin The following protected amino acids are sequentially added to the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg(Pbf)-OH, Fmoc-Val-OH, Fmoc-Ala-OH, Fmoc-Glu(OtBu)OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Asp(OtBu)-OH, Fmoc-Ser(tBu)-OH, Boc-His(Trt)-OH. They are dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (Step 1). Resin cleavage and product isolation is performed using 85% TFA/5% TIS/5% thioanisole and 5% phenol, followed by precipitation by dry-ice cold Et$_2$O (Step 2). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at 214 and 254 nm to afford the desired peptide in >95% purity, as determined by RP-HPLC.

B. Preparation of Modified Exendin 3

Using automated peptide synthesis, the following protected amino acids were sequentially added to Rink Amide MBHA resin: Fmoc-Lys(Aloc)-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp-OH, Fmoc-Glu(OtBu)-OH, Fmoc-Ile-OH, Fmoc-Phe-OH, Fmoc-Leu-OH, Fmoc-Arg(Bpf)-OH, Fmoc-Val-OH, Fmoc-Ala-OH, Fmoc Glu(OtBu)H, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Asp(OtBu)-OH, Fmoc-Ser(OtBu)-OH, Boc-His(Trt)-OH (Step 1). The modified exendin 3 is synthesized by linking off the ε-N terminus of the added lysine residue.

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 13

Preparation of Exendin-3 (1-39)-Lys$^{40}$(ε-AEEA-AEEA-MPA)-NH$_2$.5TFA;

His-Ser-Asp-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-Lys(ε-AEEA-AEEA-MPA)-NH$_2$.5TFA (SEQ ID NO:34)

The modified exendin-3 peptide is synthesized by linking off the ε-N terminus of the added Lysine residue as described below.

Using automated peptide synthesis, the following protected amino acids were sequentially added to Rink Amide MBHA resin: Fmoc-Lys(Aloc)-OH, Fmoc-Ser(tBu)OH, Fmoc-Pro-OH, Fmoc-Pro-OH, Fmoc-Pro-OH, Fmoc-Ala-OH, Fmoc-Gly-OH, Fmoc-Ser-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp-OH, Fmoc-Glu(OtBu)-OH, Fmoc-Ile-OH, Fmoc-Phe-OH, Fmoc-Leu-OH, Fmoc-Arg(Bpf)-OH, Fmoc-Val-OH, Fmoc-Ala-OH, Fmoc-Glu(OtBu)-OH, Fmoc-Glu(OtBu)-OH, Fmoc-Glu(OtBu)OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Asp(OtBu)-OH, Fmoc-Ser(OtBu)-OH, Boc-His(Trt)-OH (Step 1).

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL. The synthesis was then re-automated for the addition of the two AEEA (aminoethoxyethoxyacetic acid) groups and the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 14

Preparation of $Lys^{26}$(ε-MPA)GLP-1(7-36)-$NH_2$

His-Ala-Glu-Gly-Thr-Phe-Thr-Ser-Asp-Val-Ser-Ser-Tyr-Leu-Glu-Gly-Gln-Ala-Ala-Lys(c-MPA)-Glu-Phe-Ile-Ala-Trp-Leu-Val-Lys-Gly-Arg-$NH_2$(SEQ ID NO: 37)

Solid phase peptide synthesis of the DAC:GLP-1 analog on a 100 μmole scale is performed manually and on a Symphony Peptide Synthesizer using Fmoc protected Rink amide MBHA resin. The following protected amino acids are sequentially added to the resin: Fmoc-Arg(Pbf)-OH, Fmoc-Gly-OH, Fmoc-Lys(Boc)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Aloc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(Trt)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved

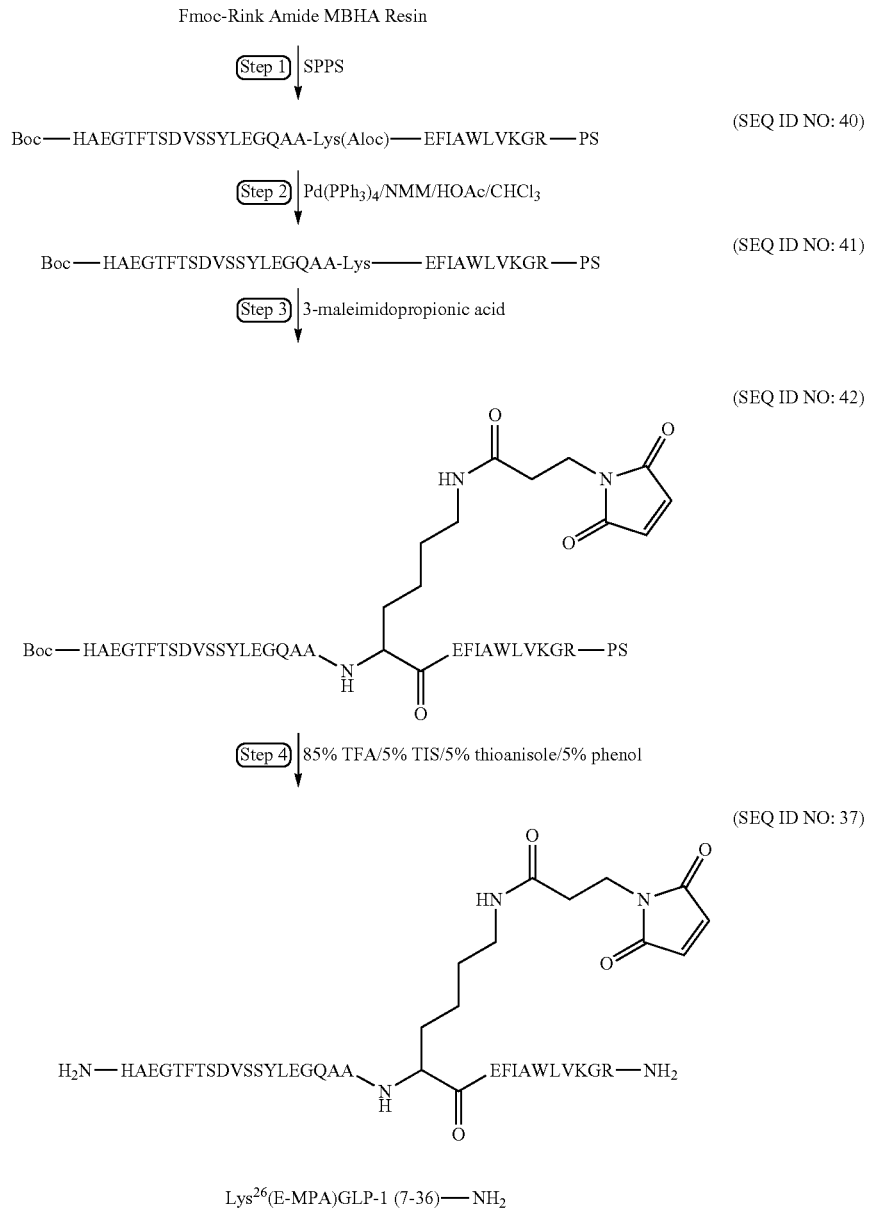

using a solution of 20% (V/V) piperidine in N,N-dimethylformamide (DMF) for 20 minutes (Step 1). Selective deprotection of the Lys(Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Resin cleavage and product isolation is performed using 86% TFA/5% TIS/5% H$_2$O/2% thioanisole and 2% phenol, followed by precipitation by dry-ice cold Et$_2$O (Step 4). The product is purified by preparative reversed phase HPLC using a Varian (Rainin) preparative binary HPLC system using a Dynamax C$_{18}$ 60 Å, 8 μm, 21 mm×25 cm column equipped with a Dynamax C$_{18}$, 60 Å, 8 μm guard module, 21 mm×25 cm column and UV detector (Varian Dynamax UVD II) at λ214 and 254 nm to afford the desired DAC in >95% purity, as determined by RP-HPLC.

OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(tBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, Boc-His(Trt)-OH, They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (Step 1). The fully protected peptide is cleaved from the resin by treatment with 1% TFA/DCM (Step 2). Ethylenediamine and 3-maleimidopropionic acid are then sequentially added to the free C-terminus (Step 3). The protecting groups are then cleaved and the product isolated using 86% TFA/5% TIS/5% H$_2$O/2% thioanisole and 2% phenol, fol-

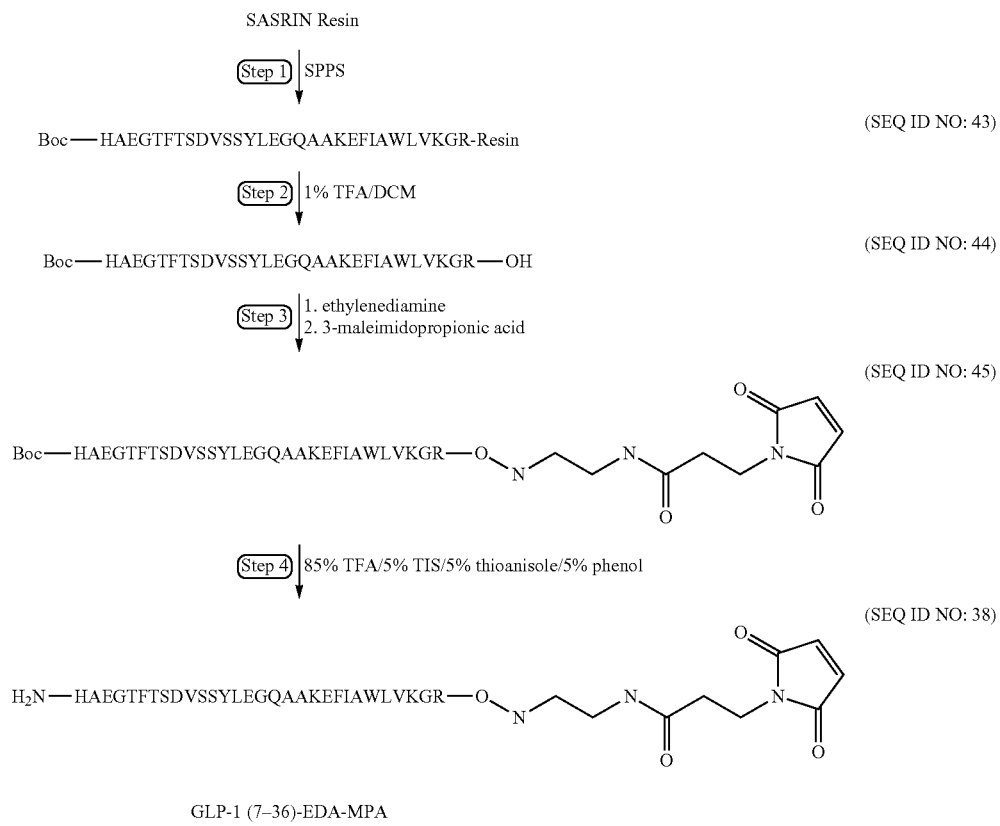

GLP-1 (7–36)-EDA-MPA

Example 15

Preparation of GLP-1 (7-36)-EDA-MPA

His-Ala-Glu-Gly-Thr-Phe-Thr-Ser-Asp-Val-Ser-Ser-Tyr-Leu-Glu-Gly-Gln-Ala-Ala-Lys(ε-MPA)-Glu-Phe-Ile-Ala-Trp-Leu-Val-Lys-Gly-Arg(EDA-MPA) (SEQ ID NO: 38)

Solid phase peptide syntheses of the modified GLP-1 analog on a 1100 μmole scale is performed manually and on a Symphony Peptide Synthesizer SASRIN (super acid sensitive resin). The following protected amino acids are sequentially added to the resin: Fmoc-Arg(Pbf)-OH, Fmoc-Gly-OH, Fmoc-Lys(Boc)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Boc)-OH, Fmoc-Alalowed by precipitation by dry-ice cold Et$_2$O (Step 4). The product is purified by preparative reversed phase HPLC using a Varian (Rainin) preparative binary HPLC system using a Dynamax C$_{18}$, 60 Å, 8 μm, 21 mm×25 cm column equipped with a Dynamax C$_{18}$, 60 Å, 8 μm guard module, 21 mm×25 cm column and UV detector (Varian Dynamax UVD II) at λ214 and 254 nm to afford the desired DAC in >95% purity, as determined by RP-HPLC.

Example 16

Preparation of Exendin-4(1-39)-EDA-MPA

His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (EDA-MPA) (SEQ ID NO: 39)

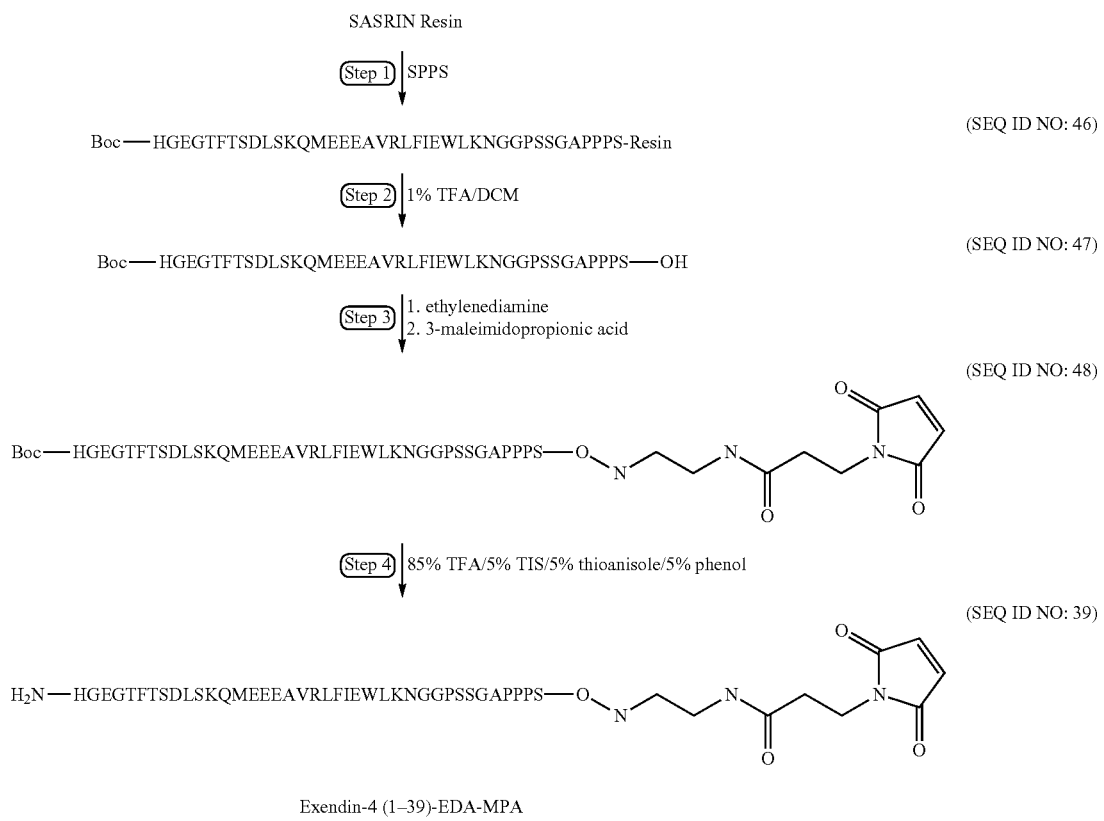

Exendin-4 (1–39)-EDA-MPA

Solid phase peptide syntheses of the modified Exendin-4 analog on a 100 µmole scale is performed manually and on a Symphony Peptide Synthesizer SASRIN (super acid sensitive resin). The following protected amino acids are sequentially added to the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg(Pbf)H, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Boc-His(T)-OH, They are dissolved in N,N-dimethylformamide (DMF) and, according to the sequence, activated using O-benzotriazol-1-yl-N, N,N', N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (Step 1). The fully protected peptide is cleaved from the resin by treatment with 1% TFA/DCM (Step 2). Ethylenediamine and 3-maleimidopropionic acid are then sequentially added to the free C-terminus (Step 3). The protecting groups are then cleaved and the product isolated using 86% TFA/5% TIS/5% $H_2O$/2% thioanisole and 2% phenol, followed by precipitation by dry-ice cold $Et_2O$ (Step 4). The product is purified by preparative reversed phase HPLC using a Varian (Rainin) preparative binary HPLC system using a Dynamax $C_{18}$, 60 Å, 8 µm, 21 mm×25 cm column equipped with a Dynamax $C_{18}$, 60 Å, 8 µm guard module, 21 mm×25 cm column and UV detector (Varian Dynamax UVD II) at λ214 and 254 nm to afford the desired DAC in >95% purity, as determined by RP-HPLC.

We claim:

1. A method for treating obesity in a subject, comprising administering to the subject a therapeutically effective amount of a compound according to the following formula:

(SEQ ID NO:36)

His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser

2. The method of claim 1, wherein said compound is in association with a physiologically acceptable medium.

3. A method for treating obesity in a subject, comprising administering to the subject a therapeutically effective amount of a conjugate formed by reacting a compound according to the following formula:

(SEQ ID NO: 36)

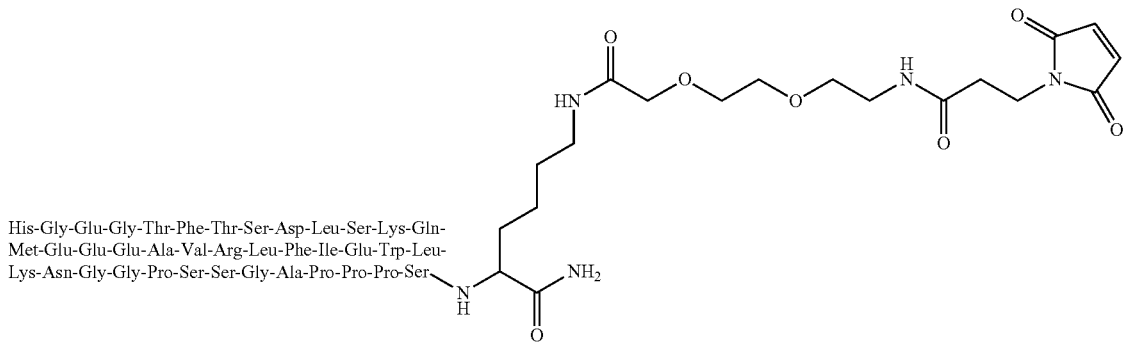

with albumin, wherein said reacting forms a covalent bond between said compound and albumin.

4. The method of claim 3, wherein said albumin is serum albumin.

5. The method of claim 3, wherein said reacting occurs between said compound and cysteine 34 thiol of albumin.

6. The method of claim 3, wherein said conjugate is in association with a physiologically acceptable medium.

7. The method of claim 4, wherein said conjugate is in association with a physiologically acceptable medium.

8. The method of claim 5, wherein said conjugate is in association with a physiologically acceptable medium.

9. A method for treating decreased insulin sensitivity in a subject, comprising administering to the subject a therapeutically effective amount of a compound according to the following formula:

(SEQ ID NO: 36)

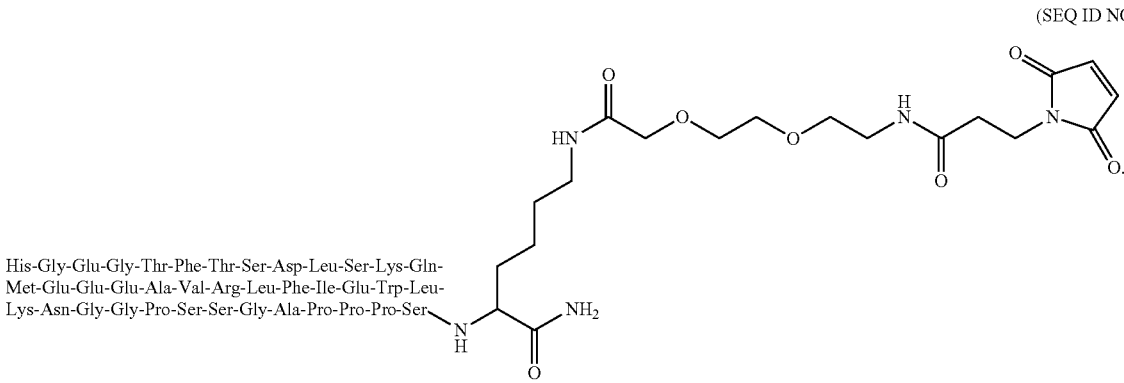

10. The method of claim 9, wherein said compound is in association with a physiologically acceptable medium.

11. A method for treating decreased insulin sensitivity in a subject, comprising administering to the subject a therapeutically effective amount of a conjugate formed by reacting a compound according to the following formula:

(SEQ ID NO: 36)

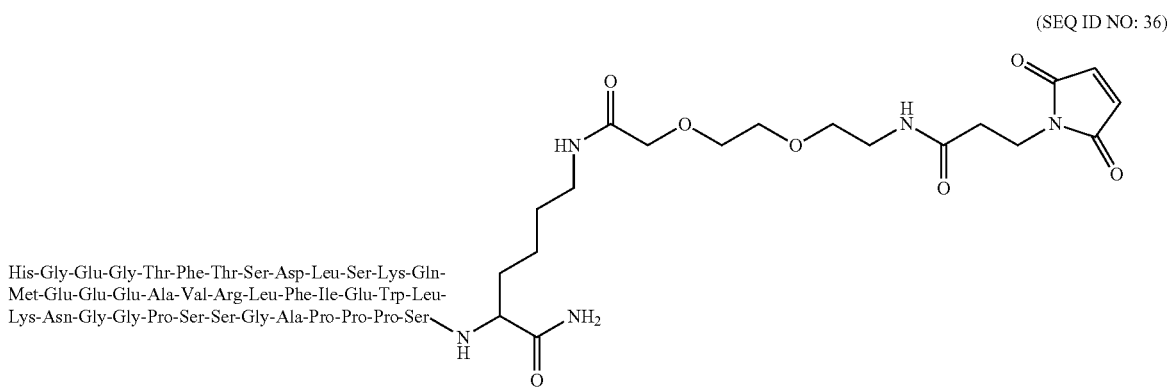

with albumin, wherein said reacting forms a covalent bond between said compound and albumin.

12. The method of claim 11, wherein said albumin is serum albumin.

13. The method of claim 11, wherein said reacting occurs said compound and cysteine 34 thiol of albumin.

14. The method of claim 11, wherein said conjugate is in association with a physiologically acceptable medium.

15. The method of claim 12, wherein said conjugate is in association with a physiologically acceptable medium.

16. The method of claim 13, wherein said conjugate is in association with a physiologically acceptable medium.

17. The method of any one of claims 1-8, wherein the subject is a human.

18. The method of any one of claims 9-16, wherein the subject is a human.

19. The method of claim 4, wherein the serum albumin is human serum albumin.

20. The method of claim 5, wherein said albumin is serum albumin.

21. The method of claim 20, wherein said conjugate is in association with a physiologically acceptable medium.

22. The method of claim 21, wherein the subject is a human.

23. The method of claim 5, wherein said albumin is human serum albumin.

24. The method of claim 23, wherein said conjugate is in association with a physiologically acceptable medium.

25. The method of claim 24, wherein the subject is a human.

26. The method of claim 12, wherein the serum albumin is human serum albumin.

27. The method of claim 13, wherein said albumin is serum albumin.

28. The method of claim 27, wherein said conjugate is in association with a physiologically acceptable medium.

29. The method of claim 28, wherein the subject is a human.

30. The method of claim 13, wherein said albumin is human serum albumin.

31. The method of claim 30, wherein said conjugate is in association with a physiologically acceptable medium.

32. The method of claim 31, wherein the subject is a human.

\* \* \* \* \*